United States Patent
Nishimura et al.

(10) Patent No.: US 10,048,249 B2
(45) Date of Patent: Aug. 14, 2018

(54) BLOOD COAGULATION ANALYZER AND BLOOD COAGULATION ANALYZING METHOD

(71) Applicant: SYSMEX CORPORATION, Kobe-shi, Hyogo (JP)

(72) Inventors: Naoto Nishimura, Kobe (JP); Tsuyoshi Fukuzaki, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 0 days.

(21) Appl. No.: 15/441,401

(22) Filed: Feb. 24, 2017

(65) Prior Publication Data

US 2017/0248576 A1 Aug. 31, 2017

(30) Foreign Application Priority Data

Feb. 29, 2016 (JP) .................... 2016-036934

(51) Int. Cl.
*G01N 33/48* (2006.01)
*G01N 33/49* (2006.01)
(Continued)

(52) U.S. Cl.
CPC ......... *G01N 33/4905* (2013.01); *G01N 15/06* (2013.01); *G01N 21/13* (2013.01); *G01N 21/255* (2013.01); *G01N 21/27* (2013.01); *G01N 21/272* (2013.01); *G01N 21/274* (2013.01); *G01N 21/314* (2013.01); *G01N 21/3151* (2013.01); *G01N 21/59* (2013.01); *G01N 21/77* (2013.01);
(Continued)

(58) Field of Classification Search
CPC .............. G01N 35/025; G01N 35/026; G01N 2035/00752; G01N 21/31; G01N 21/59; G01N 33/86; G01N 35/00603; G01N 2035/00465; G01N 35/00594; G01N 2035/0444; G01N 21/0332; G01N 21/17; G01N 2201/0231
See application file for complete search history.

(56) References Cited

U.S. PATENT DOCUMENTS 6,487,343 B1 11/2002 Lewandowski et al.
2003/0193817 A1 10/2003 Yoneda et al.
(Continued)

FOREIGN PATENT DOCUMENTS

CN 101799412 B 4/2012
EP 1890142 A2 2/2008

*Primary Examiner* — Michael P Stafira
(74) *Attorney, Agent, or Firm* — MetroLexis Law Group, PLLC

(57) ABSTRACT

A blood coagulation analyzer comprises: a light irradiation unit configured to apply light onto a container configured to store a measurement specimen containing a sample and a reagent, and comprising: light sources including a first light source configured to generate light of a first wavelength for blood coagulation time measurement, a second light source configured to generate light of a second wavelength for synthetic substrate measurement, and a third light source configured to generate light of a third wavelength for immunonephelometry measurement; and optical fiber parts facing the respective light sources; a light reception part configured to receive light transmitted through the container; and an analysis unit configured to analyze the sample using an electric signal outputted from the light reception part.

25 Claims, 13 Drawing Sheets

(51) Int. Cl.

| | | |
|---|---|---|
| *G01N 15/06* | (2006.01) | |
| *G01N 21/13* | (2006.01) | |
| *G01N 21/25* | (2006.01) | |
| *G01N 21/27* | (2006.01) | |
| *G02B 6/42* | (2006.01) | |
| *G01N 21/31* | (2006.01) | |
| *G01N 21/59* | (2006.01) | |
| *G01N 21/77* | (2006.01) | |
| *G01N 21/78* | (2006.01) | |
| *F21V 8/00* | (2006.01) | |
| *G01N 33/86* | (2006.01) | |

(52) U.S. Cl.
CPC ........... *G01N 21/78* (2013.01); *G01N 33/492* (2013.01); *G01N 33/86* (2013.01); *G02B 6/0008* (2013.01); *G02B 6/4204* (2013.01); *G02B 6/4228* (2013.01); *G01N 2015/0693* (2013.01); *G01N 2021/135* (2013.01); *G01N 2021/3148* (2013.01); *G01N 2021/3181* (2013.01); *G01N 2021/3188* (2013.01); *G01N 2021/7783* (2013.01); *G01N 2201/0631* (2013.01); *G01N 2201/06153* (2013.01); *G01N 2201/0826* (2013.01)

(56) References Cited

U.S. PATENT DOCUMENTS

| | | |
|---|---|---|
| 2007/0037272 A1 | 2/2007 | Beatty et al. |
| 2007/0248490 A1 | 10/2007 | Matsuo et al. |
| 2008/0044912 A1 | 2/2008 | Yamamoto et al. |
| 2008/0070318 A1* | 3/2008 | Yamamoto ............. G01N 21/31 436/164 |
| 2008/0158552 A1 | 7/2008 | Tokunaga et al. |
| 2015/0304027 A1* | 10/2015 | Nciri ......................... G01J 3/10 398/119 |
| 2015/0346092 A1 | 12/2015 | Lee et al. |

* cited by examiner

BLOOD COAGULATION ANALYZER AND BLOOD COAGULATION ANALYZING METHOD

CROSS REFERENCE TO RELATED APPLICATIONS

This application claims priority under 35 U.S.C. § 119 from prior Japanese Patent Application No. 2016-036934 filed on Feb. 29, 2016, entitled "BLOOD COAGULATION ANALYZER AND BLOOD COAGULATION ANALYZING METHOD", the entire contents of which are hereby incorporated herein by reference.

FIELD OF THE INVENTION

The disclosure relates to a blood coagulation analyzer and a blood coagulation analyzing method.

BACKGROUND

US 2008/044912 (Patent Document 1) discloses a blood coagulation analyzer in which a light irradiation unit applies light having different wavelengths for blood coagulation analysis onto a measurement container installed in a container installation section, and a light reception part detects light transmitted through the measurement container. The light irradiation unit in Patent Document 1 includes a halogen lamp that is a broadband light source and a filter unit that holds optical filters having different transmittance wavelengths along the circumference. The filter unit is configured to rotate the optical filters around the central axis and to sequentially dispose the optical filters on an optical path from a light source. Thus, the light irradiation unit sequentially applies light having different wavelengths onto the measurement container installed in the container installation section. The light having the different wavelengths is used to measure a sample in different measurement items.

SUMMARY

One or more embodiments of a blood coagulation analyzer may comprise: a light irradiation unit configured to apply light onto a container configured to store a measurement specimen containing a sample and a reagent, and comprising: light sources including a first light source configured to generate light of a first wavelength for blood coagulation time measurement, a second light source configured to generate light of a second wavelength for synthetic substrate measurement, and a third light source configured to generate light of a third wavelength for immunonephelometry measurement; and optical fiber parts facing the respective light sources; a light reception part configured to receive light transmitted through the container; and an analysis unit configured to analyze the sample using an electric signal outputted from the light reception part.

One or more embodiments of a blood coagulation analyzing method may comprise: generating light from light sources including a first light source configured to generate light of a first wavelength for blood coagulation time measurement, a second light source configured to generate light of a second wavelength for synthetic substrate measurement, and a third light source configured to generate light of a third wavelength for immunonephelometry measurement; making the lights from the light sources incident on incident ends of optical fiber parts facing the respective light sources; applying light emitted from each of exit ends of the optical fiber parts onto a container configured to contain a measurement specimen storing a sample and a reagent; and detecting light transmitted through the container so as to analyze the sample using the detected light.

EMBODIMENTS

With reference to the drawings, an embodiment is described below.

[Overview of Blood Coagulation Analyzer]

Figure 1:
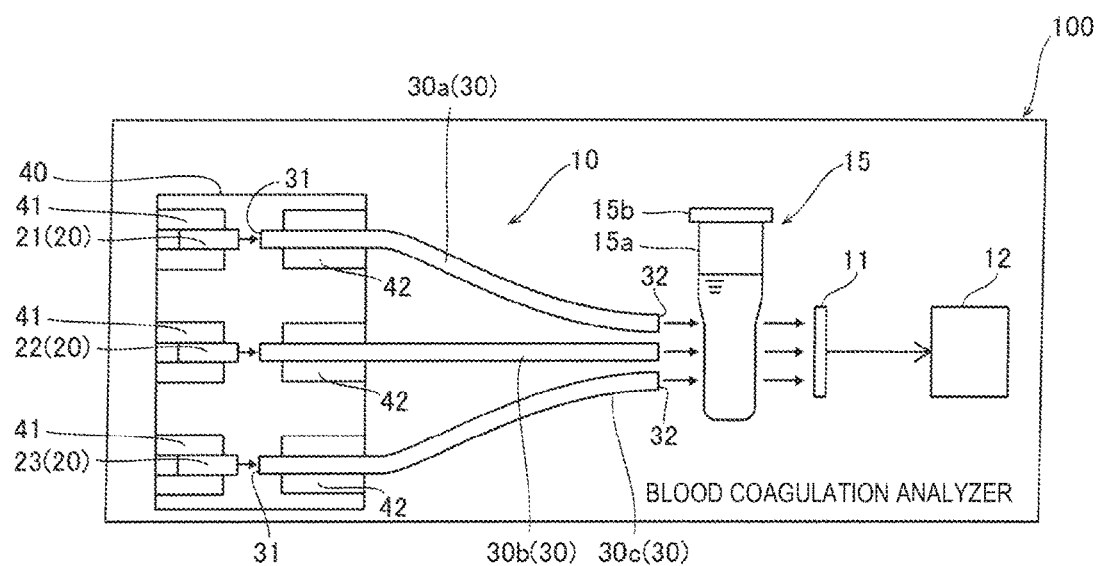
FIG. 1 is a schematic view illustrating an overview of a blood coagulation analyzer according to an embodiment.

As illustrated in FIG. 1, blood coagulation analyzer 100 applies light onto a measurement specimen prepared by adding a reagent to a sample, detects transmitted light or scattered light of the light applied onto the measurement specimen, and analyzes the sample using the detected light. The sample is a plasma or serum separated from blood. Blood coagulation analyzer 100 analyzes the sample using a coagulation method, a synthetic substrate method, immunonephelometry or an agglutination method.

Blood coagulation analyzer 100 includes: light irradiation unit which applies light onto container 15 that stores the measurement specimen containing the sample and the reagent; light reception part 11, or a light receptor, for detecting the light applied by light irradiation unit 10 and transmitted through container 15; and analysis unit 12 for analyzing the sample using an electric signal to be outputted from light reception part 11.

Container 15 is a cuvette for storing the measurement specimen having the sample and the reagent mixed therein. Container 15 is made of translucent resin, glass or the like, and is preferably transparent enough not to affect the applied light. Container 15 has a top-opened and bottom-closed cylindrical shape, for example. In FIG. 1, container 15 includes top-opened cylindrical body section 15a and flange section 15b provided at an upper end of body section 15a. Body section 15a has its lower part smaller in diameter than its upper part. The shape of container 15 is not limited to the one illustrated in FIG. 1.

Light irradiation unit 10 includes light sources 20 and optical fiber parts 30 provided facing respective light sources 20. Note that light irradiation unit 10 may further include holding member 40 for holding light sources 20 and respective incident ends 31 of optical fiber parts 30. With holding member 40 provided, light sources 20 and incident ends 31 of optical fiber parts 30 can be more easily held. Alternatively, sets of light sources 20 and incident ends 31 may be individually fixed without providing holding member 40.

Light sources 20 include light sources for use in blood coagulation analysis. To be more specific, light sources 20 include: first light source 21 for generating light having a first wavelength for measuring a blood coagulation time; second light source 22 for generating light having a second wavelength for measuring a synthetic substrate; and third light source 23 for generating light having a third wavelength for immunonephelometry measurement. The light sources 20 may further include light sources other than first light source 21, second light source 22, and third light source 23.

Each of light sources 20 generates light having a predetermined wavelength corresponding to the measurement item. As the light having the first wavelength to be generated by first light source 21, light in a wavelength band of 620 nm to 690 nm, more preferably, light in a wavelength band of 630 nm to 680 nm can be used, for example. As for the first wavelength, a predetermined wavelength suitable for the reagent to be added to the sample is selected, which is 660 nm, for example. In the coagulation method, the light having the first wavelength is applied onto the measurement specimen. A coagulation time required for fibrinogen in the sample to be converted to fibrin is measured using an electric signal of transmitted light or scattered light from the specimen. Examples of the measurement item for the coagulation method include PT (prothrombin time), APTT (activated partial thromboplastin time), Fbg (fibrinogen amount), and the like.

As the light having the second wavelength to be generated by second light source 22, light in a wavelength band of 390 nm to 420 nm, more preferably, light in a wavelength band of 400 nm to 410 nm can be used, for example. The second wavelength is 405 nm, for example. In the synthetic substrate method, the light having the second wavelength is applied onto the measurement specimen. A degree of coloring by the action of a chromogenic synthetic substrate on the enzyme in the measurement specimen is measured using an electric signal of transmitted light from the specimen. Examples of the measurement item for the synthetic substrate method include ATIII (antithrombin III), α2-PI (plasmin inhibitor), PLG (plasminogen), and the like.

As the light having the third wavelength to be generated by third light source 23, light in a wavelength band of 690 nm to 820 nm, more preferably, light in a wavelength band of 700 nm to 810 nm can be used, for example. The third wavelength is 800 nm, for example. In the immunonephelometry, a reagent that causes an antigen-antibody reaction of a coagulation-fibrinolysis factor and the like in a sample is added to the sample, and substances contained in the reagent are agglutinated as a result of the antigen-antibody reaction. The light having the third wavelength is applied onto the measurement specimen. An agglutination rate of the substances contained in the reagent in the measurement specimen is measured using an electric signal of transmitted light or scattered light from the specimen. Examples of the measurement item for the immunonephelometry include a D-dimer, FDP (fibrin degradation products), and the like.

By providing light sources 20 individually corresponding to the respective measurement items, light sources each generating light in a narrow wavelength band around the wavelength for use in measurement can be adopted, rather than a broadband light source that covers a wide wavelength band, such as a halogen lamp. As for first light source 21, for example, a light source including the first wavelength and hardly including the second and third wavelengths can be adopted. Therefore, as light sources 20, relatively narrow-band light sources, each including the wavelength for use in measurement as a center wavelength, can be used. For example, a semiconductor light emitting element such as an LED (light emitting diode) and a semiconductor laser can be used.

Each of optical fiber parts 30 has a cable-shaped structure including incident end 31 and exit end 32. Optical fiber part 30 has a function to guide light applied onto incident end 31 to exit end 32. Optical fiber part 30 includes one or more optical fibers.

Optical fiber parts 30 are provided corresponding to respective light sources 20. More specifically, one optical fiber part 30 is provided to each of light sources 20. In the configuration example illustrated in FIG. 1, optical fiber parts 30 include optical fiber part 30a corresponding to first light source 21, optical fiber part 30b corresponding to second light source 22, and optical fiber part 30c corresponding to third light source 23. When light sources 20 include light sources other than first to third light sources 21 to 23, additional optical fiber parts corresponding to those light sources are provided.

In the configuration further including holding member 40, holding member 40 has a function to hold light sources 20 and incident ends 31 of optical fiber parts 30, thereby maintaining a positional relationship therebetween. Holding member 40 includes, for example: light source holders 41 which hold respective light sources 20; and incident end holders 42 which are provided at positions facing respective light sources 20 held by respective light source holders 41, and which hold incident ends 31 of optical fiber parts 30. Thus, holding member 40 hold light sources 20 and incident ends 31 of optical fiber parts 30 in a state of facing each other. Light source holder 41 and incident end holder 42 are provided for each pair of one light source 20 and incident end 31 of optical fiber part 30 corresponding to that light source 20. Also, light source holder 41 and incident end holder 42 hold each light source 20 and incident end 31 of corresponding optical fiber part 30 at positions close to each other. Holding member 40 hold light source 20 and optical fiber part 30 in a state where an optical axis of light source 20 and a central axis of optical fiber part 30 almost coincide with each other. Instead of providing holding member 40, a set of light source holder 41 and incident end holder 42 may be individually provided for each pair of light source 20 and incident end 31.

Light reception part 11 includes a photoelectric conversion element that converts received light into an electric signal and outputs the electric signal. Blood coagulation analyzer 100 may include an amplifier circuit that amplifies the electric signal outputted from the photoelectric conversion element in light reception part 11. Light reception part 11 has a function to output an electric signal depending on the amount of light received to analysis unit 12. Light reception part 11 is disposed facing exit ends 32 of optical fiber parts 30, for example. By disposing container 15 storing the measurement specimen between light reception part 11 and exit ends 32, light reception part 11 detects light applied from light irradiation unit 10 and transmitted through container 15. The light transmitted through container 15 is transmitted light or scattered light of the light applied onto the measurement specimen. The transmitted light or scattered light of the light applied onto the specimen is transmitted through container 15 and received by light reception part 11. Light reception part 11 may be configured to receive both of the transmitted light and scattered light.

Note that FIG. 1 illustrates the configuration example in which exit light from exit ends 32 of optical fiber parts 30 is applied directly onto container 15, transmitted through container 15 and received by light reception part 11. Alternatively, another optical element may be provided between exit ends 32 of optical fiber parts and light reception part 11. For example, when light is applied onto more than one container 15, an optical element for distributing the light from exit ends 32 of optical fiber parts 30 to containers may be provided. Alternatively, a lens or optical filter having certain optical characteristics may be disposed just before container or between container 15 and light reception part 11.

Analysis unit 12 includes a computer with a processor, a memory, and the like. Analysis unit 12 may cause a general-purpose computer to execute a sample analysis program, or may use dedicated hardware. Analysis unit 12 records data on electric signals to be outputted from light reception part 11, and analyzes the sample in reference to the measurement item. A change in the electric signal outputted from light reception part 11 represents a change in the amount of light received by light reception part 11. In measurements using first to third light sources 21 to 23 described above, analysis unit 12 can analyze the sample on the basis of a change in the electric signal outputted from light reception part 11 during a predetermined measurement time. In the case of the coagulation method, analysis unit 12 analyzes the blood coagulation time. In the case of the synthetic substrate method, analysis unit 12 analyzes a change in absorbance during the process of coloring by the chromogenic synthetic substrate. In the case of the immunonephelometry, analysis unit 12 analyzes a change in absorbance due to an antigen-antibody reaction of a reagent. In the case of analysis using other measurement methods, again, analysis unit 12 analyzes the sample on the basis of an electric signal in reference to the measurement methods.

Next, description is given of an analysis method using blood coagulation analyzer 100. In blood coagulation analyzer 100, light sources 20 held by holders 40 generate light. In blood coagulation analyzer 100, light from light sources 20 is made incident on respective incident ends 31 of optical fiber parts 30 held by holders 40. Then, in blood coagulation analyzer 100, exit light from exit ends 32 of optical fiber parts 30 is applied onto container 15 storing the sample, and the light transmitted through container 15 is detected. Blood coagulation analyzer 100 analyzes the sample using the detected light.

With the above configuration, blood coagulation analyzer 100 can perform a blood coagulation analysis using small and long-life light sources 20 such as LEDs, rather than a combination of a broadband light source such as a halogen lamp and a rotary filter device, by providing light sources 20 and optical fiber parts 30 corresponding to light sources 20. This makes it possible to extend the life of the light sources compared with the halogen lamp, and to suppress an increase in size of the analyzer configuration. Furthermore, unlike a configuration in which a mirror is disposed in an optical path from light sources 20 to guide light to container 15, light source holders 41 and incident end holders 42 of holding member 40 can hold light sources 20 and incident ends 31 of optical fiber parts 30 at close positions where light sources 20 and incident ends 31 face each other. Thus, optical axis alignment can be easily and accurately performed. As a result, it is possible to suppress an increase in size of the configuration of blood coagulation analyzer 100 which applies light having different wavelengths for blood coagulation analysis. Moreover, the life of the light sources can be extended and the occurrence of optical axis misalignment can be easily suppressed.

Also, since light sources 20 and incident ends 31 of optical fiber parts 30 can be held at the positions close to each other, light to be lost before the light applied from light sources 20 enters optical fiber parts 30 can be reduced. Thus, the influence of noise to be mixed into the electric signal to be outputted from light reception part 11 can be reduced. As a result, a highly reproducible blood coagulation analysis result can be obtained. For example, when a coagulation time is calculated with a percentage detection method as the blood coagulation analysis result, a large influence of noise to be mixed into the electric signal to be outputted from light reception part 11 may lead to a situation where coagulation times calculated differ from one measurement to another even if the same sample is measured more than once. On the other hand, since light sources 20 and incident ends 31 of optical fiber parts 30 can be held at the positions close to each other in blood coagulation analyzer 100, the influence of noise to be mixed into the electric signal to be outputted from light reception part 11 can be reduced. Thus, when the coagulation time is calculated with the percentage detection method as the blood coagulation analysis result, for example, a highly reproducible coagulation time can be obtained.

[Configuration Example of Blood Coagulation Analyzer]

Figure 2:
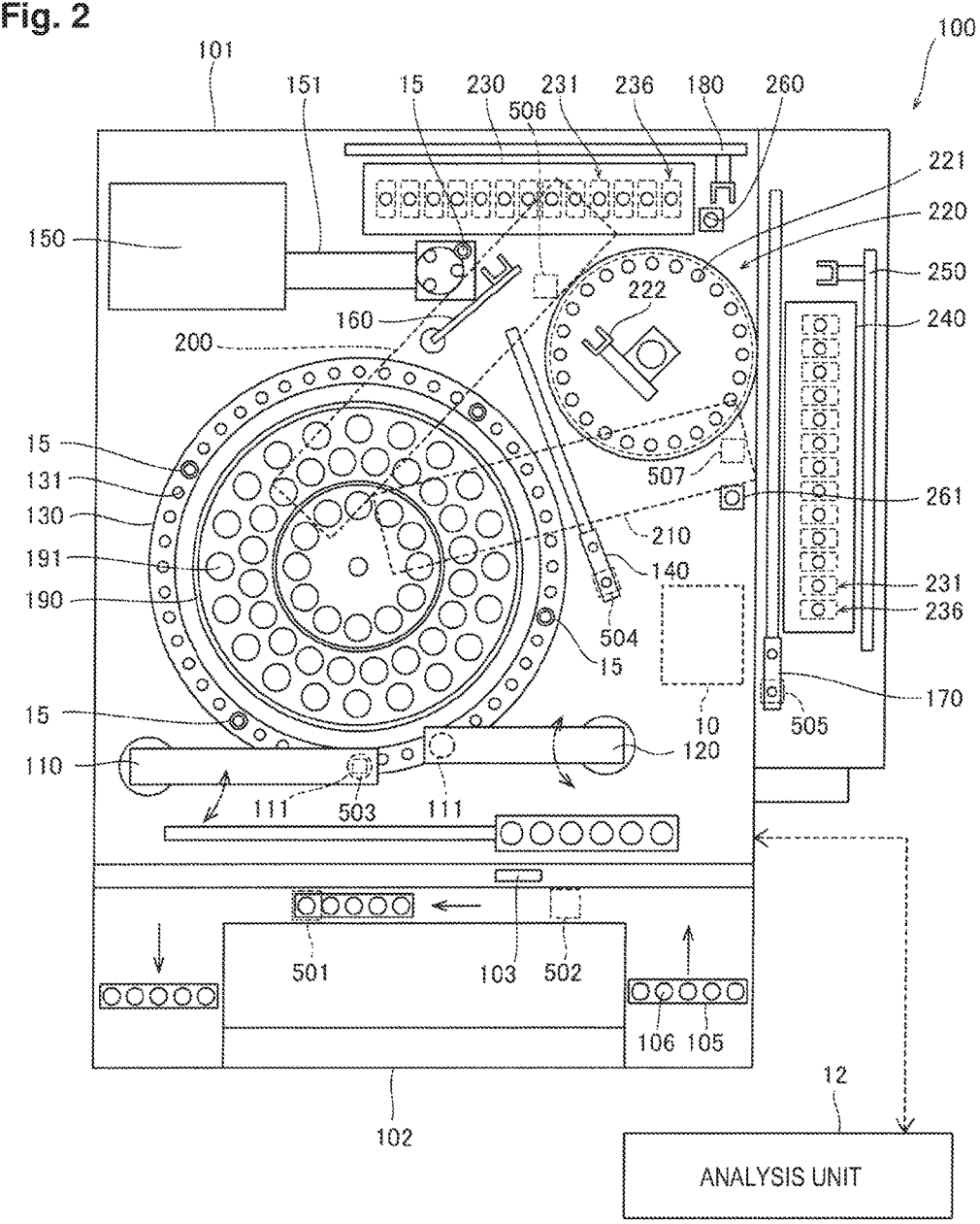
FIG. 2 is a schematic plan view for explaining an example of an overall configuration of the blood coagulation analyzer.

With reference to FIGS. 2 to 16, description is given below of a more specific configuration example of blood coagulation analyzer 100 illustrated in FIG. 1. FIG. 2 illustrates a configuration example of an automatic analyzer for blood coagulation analysis.

(Overall Configuration)

In the configuration example of FIG. 2, blood coagulation analyzer 100 includes measurement unit 101, transport unit 102, and analysis unit 12. Light irradiation unit 10 and light reception part 11 (see FIG. 9) are provided in measurement unit 101.

In the configuration example of FIG. 2, blood coagulation analyzer 100 has a function to aspirate a sample from a sample container that stores the sample, and to dispense a measured amount of the sample into container 15.

Sample rack 105 is set in transport unit 102. In sample rack 105, sample containers 106, each storing a sample, can be installed. Transport unit 102 transports sample rack 105 set by a user to position each of sample containers 106 at predetermined sample aspirating position 501 or 502. Labels (not illustrated) having identification information recorded on barcodes and the like are attached to sample rack 105 and sample containers 106. The identification information on sample rack 105 and sample containers 106 is read by reader 103 installed on a transport path, and is transmitted to analysis unit 12. With the identification information, the samples in sample containers 106 and measurement results on the samples are managed in association with each other.

Measurement unit 101 includes sample dispensers 110 and 120 for aspirating the sample in each of sample containers 106 and dispensing a measured amount of the sample into container 15.

Sample dispensers 110 and 120 each include a dispensing arm that rotatably holds pipette 111 for dispensing the sample. Pipette 111 is connected to an unillustrated pump, and can aspirate and dispense a measured amount of the sample. Sample dispenser 110 can aspirate a predetermined amount of the sample from sample container 106 at sample aspirating position 501 with moving pipette 111. Sample dispenser 120 can aspirate a predetermined amount of the sample from sample container 106 at sample aspirating position 502 with moving pipette 111. Each of sample dispensers 110 and 120 can dispense the aspirated sample into container 15 set at a predetermined sample dispensing position with moving pipette 111.

Measurement unit 101 performs optical measurement on a measurement specimen prepared by adding a predetermined reagent to the sample aspirated by sample dispenser 110. Alternatively, blood coagulation analyzer 100 may be configured to perform measurement on container 15 into which a measured amount of sample is dispensed in advance, without including transport unit 102 and sample dispenser 110.

Measurement unit 101 has a mechanism for transferring container storing the sample and the reagent to prepare the measurement specimen to various units. In the configuration example of FIG. 2, measurement unit 101 includes container table 130. Container table 130 has a ring shape in a planar view, and can be rotated in a circumferential direction. Container table 130 includes retention holes 131 arranged along the circumferential direction. One container can be set in each of retention holes 131. Sample dispenser 110 can dispense the aspirated sample into new container 15 held on container table 130 at sample dispensing position 503. Sample dispenser 120 can also aspirate the sample from container 15 storing the sample on container table 130.

Measurement unit 101 includes transfer unit 140 that positions new container 15 at sample dispensing position 504. Transfer unit 140 can move an installation table along a rail, the installation table including retention holes for installing container 15. Two retention holes are provided, for example. Sample dispenser 120 can dispense the aspirated sample into new container 15 held by transfer unit 140 at sample dispensing position 504.

Many new containers 15 are stored in container storage unit 150, and are taken one by one out of container storage unit 150 by container feeder 151. Container 15 taken out by container feeder 151 is caught and taken out by catcher mechanism 160. Catcher mechanism 160 can set container 15 taken out into retention hole 131 in container table 130 or the retention hole in transfer unit 140.

Measurement unit 101 includes transfer unit 170. Transfer unit 170 can move an installation table along a rail, the installation table including retention holes as in the case of transfer unit 140. New container 15 in container feeder 151 is taken out by catcher mechanism 180, and is set in the retention hole in transfer unit 170. Transfer unit 170 can transfer new container 15 thus set to sample dispensing position 505. Sample dispenser 120 can dispense the aspirated sample into new container 15 held by transfer unit 170 at sample dispensing position 505.

In the configuration example of FIG. 2, blood coagulation analyzer 100 has a function to prepare a measurement specimen by adding a reagent to a sample in container 15. The measurement specimen is a liquid mixture of the sample and the reagent.

Measurement unit 101 includes: reagent table 190 for housing reagent containers 191 for use in measurement; and reagent dispensers 200 and 210 for dispensing and aspirating reagents from the reagent containers set on reagent table 190.

Reagent table 190 is disposed on the inside of container table 130, and has a circular shape in a planar view. On reagent table 190, reagent containers 191 can be set along the circumferential direction. Reagent table 190 can be rotated in the circumferential direction, and any container 191 can be positioned at a predetermined reagent aspirating position by the rotation of reagent table 190.

Reagent dispensers 200 and 210 each include a pipette (not illustrated) for dispensing the reagent. The pipette is connected to an unillustrated pump, and can aspirate and dispense a measured amount of the reagent. Reagent dispenser 200 can aspirate a predetermined amount of the reagent from reagent container 191 positioned at a predetermined reagent aspirating position on reagent table 190. Reagent dispenser 200 can dispense the predetermined amount of reagent into container 15 at reagent dispensing position 506 with moving the pipette to reagent dispensing position 506.

Reagent dispenser 210 can aspirate a predetermined amount of the reagent from reagent container 191 positioned at a predetermined reagent aspirating position on reagent table 190. Reagent dispenser 210 can dispense the predetermined amount of reagent into container at reagent dispensing position 507 with moving the pipette to reagent dispensing position 507.

Measurement unit 101 includes heating table 220 for holding and heating container 15 into which the sample is dispensed. Heating table 220 includes: retention holes 221 for holding containers 15, each storing the sample; and catcher mechanism 222 for catching and transferring container 15. Heating table 220 includes a built-in heater (not illustrated) for heating containers 15 held in respective retention holes 221.

Heating table 220 has a circular shape in a planar view, and has retention holes 221 arranged along the circumferential direction. Heating table 220 can be rotated in the circumferential direction, and can transfer containers 15 set in retention holes 221 in the circumferential direction by its rotation while heating the containers to a predetermined temperature by the heater. Catcher mechanism 222 can catch and transfer container 15, set container 15 in retention hole 221 and take container 15 out of retention hole 221.

Catcher mechanism 222 can transfer containers 15 set in transfer unit 140 to retention holes 221 in heating table 220. Also, catcher mechanism 222 can take out containers 15 heated in retention hole 221 in heating table 220, and transfer containers 15 to reagent dispensing positions 506 and 507. Catcher mechanism 222 returns containers 15, into which the reagent is dispensed by reagent dispenser 200, to retention holes 221 in heating table 220.

Blood coagulation analyzer 100 may be configured to perform measurement on container 15 storing the measurement specimen prepared in advance, without including reagent table 190, reagent dispenser 200, and heating table 220.

Measurement unit 101 includes detection units 230 and 240 for performing optical measurement on the measurement specimen in container 15. Two detection units 230 and 240 have the same configuration. Only either one of detection units 230 and 240 may be provided. Each of detection units 230 and 240 includes: container installation sections 231 for installing containers 15, each storing a sample; and light reception parts 11 provided corresponding to container installation sections 231.

In the configuration example of FIG. 2, detection units 230 and 240 each include more than one container installation section 231. Each of detection units 230 and 240 linearly extends along one side of blood coagulation analyzer 100 in a planar view, and includes container installation sections 231 linearly arranged therein at predetermined intervals.

Measurement unit 101 includes catcher mechanisms 180 and 250 for transferring containers 15 to detection units 230 and 240, respectively.

Each of catcher mechanisms 180 and 250 includes a transfer mechanism (not shown) in three axis directions, X, Y, and Z, orthogonal to each other, and can catch and transfer containers 15. Catcher mechanism 180 can transfer container 15 between container feeder 151 and transfer unit 170 described above. Catcher mechanism 180 can take container 15 out of retention hole 221 in heating table 220, transfer container 15 to reagent dispensing position 506, and set container having the reagent dispensed thereinto in container installation section 231 in detection unit 230. Catcher mechanism 250 can take container 15 out of retention hole 221 in heating table 220, transfer container 15 to reagent dispensing position 507, and set container having the reagent dispensed thereinto in container installation section 231 in detection unit 240. Note that catcher mechanisms 180 and 250 can take containers 15 having undergone the measurement out of container installation sections 231 and transfer containers 15 to disposal ports 260 and 261, respectively.

Optical measurement is performed on the measurement specimens in containers 15 installed in container installation sections 231 in detection units 230 and 240. Light irradiation unit 10 applies measurement light onto containers 15 installed in container installation sections 231 in detection units 230 and 240. Each of light reception parts 11 (see FIG. 9) receives transmitted light or scattered light of the light applied onto container 15, and outputs an electric signal depending on the amount of light received. The electric signal is transmitted to analysis unit 12. Analysis unit 12 analyzes the sample using the electric signal outputted from light reception part 11.

(Configuration Example of Light Irradiation Unit)

Figure 3:
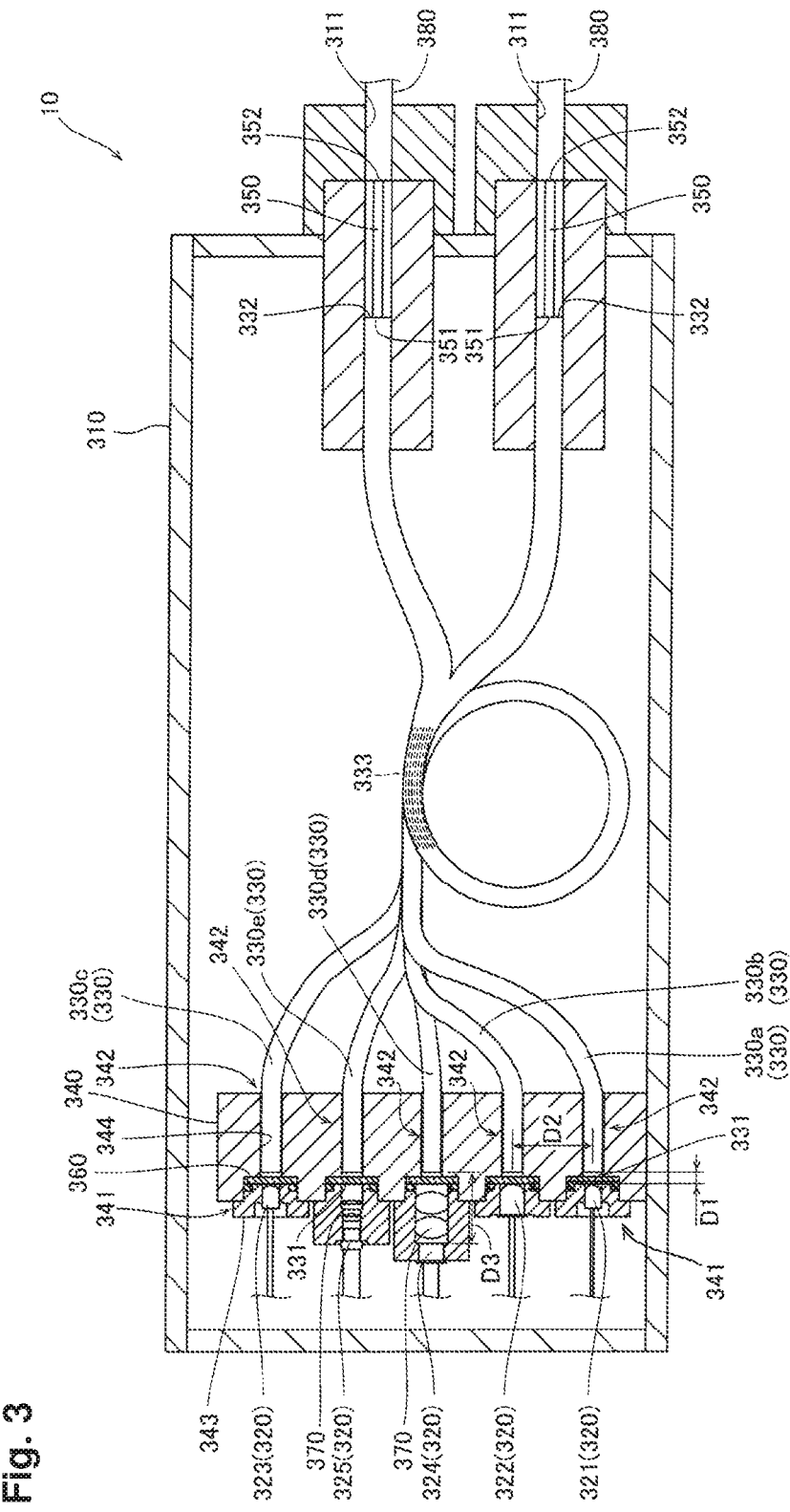
FIG. 3 is a schematic cross-sectional view illustrating a specific configuration example of a light irradiation unit.
Figure 4:
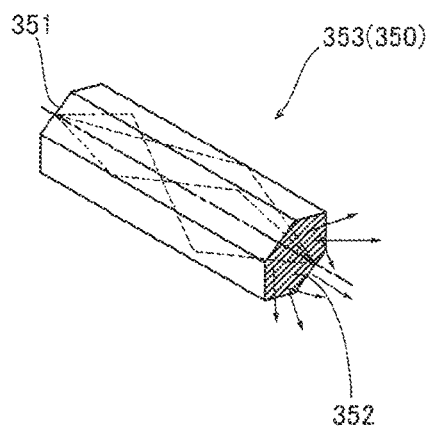
FIG. 4 is a perspective view illustrating a configuration example of a homogenization member.

FIG. 3 illustrates a configuration example of light irradiation unit 10. In the configuration example of FIG. 3, light irradiation unit 10 includes: five light sources 320; five optical fiber parts 330 provided corresponding to five light sources 320; and one holding member 340 for holding light sources 320 and incident ends 331 of optical fiber parts 330. Light sources 320, optical fiber parts 330, and holding member 340 are housed in metal housing 310, for example.

Five light sources 320 each include an LED, which generally has a life tens of times longer than a halogen lamp. Thus, smaller and longer life light irradiation unit 10 can be configured, compared with a configuration using a broadband light source such as a halogen lamp and a rotary filter. Moreover, the LEDs can be provided individually for each wavelength. Thus, an emission spectrum and an emission intensity of each of light sources 320 can be individually optimized.

Light sources 320 include first light source 321, second light source 322, and third light source 323. In the configuration example of FIG. 3, first light source 321 is a light source for measuring a blood coagulation time, which generates light having a first wavelength of about 660 nm. Second light source 322 is a light source for measuring a synthetic substrate, which generates light having a second wavelength of about 405 nm. Third light source 323 is a light source for immunonephelometry measurement, which generates light having a third wavelength of about 800 nm.

In the configuration example of FIG. 3, light sources 320 further include fourth light source 324 for generating light having a fourth wavelength different from the second wavelength for synthetic substrate measurement. The fourth wavelength is selected from a range of 300 nm to 380 nm, as in the case of the second wavelength. More preferably, light in a wavelength band of 320 nm to 360 nm can be used. In the configuration example of FIG. 3, the fourth wavelength is 340 nm, for example. The light having the fourth wavelength can be used as a sub-wavelength for synthetic substrate measurement. More specifically, an electric signal corresponding to the light having the second wavelength is compared with an electric signal corresponding to the light having the fourth wavelength. Then, the signal yielding a more stable detection result can be adopted for analysis. Thus, analysis can be performed with a more reliable electric signal. Even in such a case, it is possible to suppress an increase in size of the analyzer configuration.

In the configuration example of FIG. 3, light sources 320 further include fifth light source 325 for generating light having a fifth wavelength different from the third wavelength for immunonephelometry measurement. The fifth wavelength is selected from a range of 550 nm to 590 nm, as in the case of the third wavelength. More preferably, light in a wavelength band of 560 nm to 580 nm can be used. In the configuration example of FIG. 3, the fifth wavelength is 575 nm, for example. The light having the fifth wavelength can be used as a sub-wavelength for immunonephelometry measurement. More specifically, an electric signal corresponding to the light having the third wavelength is compared with an electric signal corresponding to the light having the fifth wavelength. Then, the signal yielding a more stable detection result can be adopted for analysis. Thus, analysis can be performed with a more reliable electric signal. Even in such a case, it is possible to suppress an increase in size of the analyzer configuration.

Optical fiber parts 330 are provided corresponding to respective light sources 320. Five optical fiber parts 330 include optical fiber parts 330a, 330b, 330c, 330d, and 330e individually provided for each of light sources 320 such that light from first to fifth light sources 321 to 325 enter incident ends 331, respectively.

In the configuration example of FIG. 3, optical fiber parts 330 each include optical fibers 333. Optical fiber parts 330 are mixed and bundled such that optical fibers 333 corresponding to respective light sources 320 are approximately evenly distributed at exit ends 332. Here, the "optical fiber" means an optical fiber strand or optical fiber core wire with one core. Each of optical fiber parts 330 is configured as a cable or a twisted wire obtained by bundling strands together. Such a configuration allows the light having various wavelengths separately entering incident ends 331 of optical fiber parts 330 to exit from common exit ends 332 rather than to be individually applied onto container 15. Thus, the configuration for exiting of the light having various wavelengths can be simplified. Moreover, the light having various wavelengths can be allowed to exit from common exit ends 332 in a state where a distribution of the light is uniform. Thus, the distribution of light for each wavelength can be prevented from being biased even when the light having various wavelengths exit from common exit ends 332.

In the configuration example of FIG. 3, five optical fiber parts 330 are twisted together in the middle and integrated so as to have two exit ends 332. Two exit ends 332 are provided corresponding to two detection units 230 and 240 (see FIG. 2), respectively. Two exit ends 332 are connected to two ejection ports 311 provided in housing 310, respectively. Each of exit ends 332 includes approximately the same number of optical fibers 333 of all optical fiber parts 330. Also, optical fibers 333 of all optical fiber parts 330 are mixed in an approximately even distribution within each of end faces of exit ends 332. The number of optical fibers 333 included in respective optical fiber parts 330 is determined on the basis of the number of container installation sections 231 in detection units 230 and 240. For example, when each of optical fiber parts 330 transmits an amount of light corresponding to M optical fibers to one container installation section 231 assuming that the number of container installation sections 231 is N, each optical fiber part 330 includes N×M optical fibers 333. Each of exit ends 332 is configured by gathering (N×M)/2 optical fibers 333 from among optical fiber parts 330.

<Homogenization Member>

In the configuration example of FIG. 3, light irradiation unit further includes homogenization members 350. Homogenization members 350 are disposed adjacent to exit ends 332 of optical fiber parts 330, and homogenize an intensity distribution of light entering from the exit end 332 side. Here, individual optical fibers 333 disposed at exit ends 332 emit light having only any of the first to fifth wavelengths. More specifically, luminous points for the wavelengths are evenly dispersed at each exit end 332. Therefore, the light from the exit end 332 is made incident on homogenization member 350 and thus homogenized. Accordingly, on exit plane 352 of homogenization member 350, the intensity distribution of each wavelength is homogenized across the entire plane. Thus, a variation in light intensity for each wavelength can be effectively homogenized.

Figure 6:
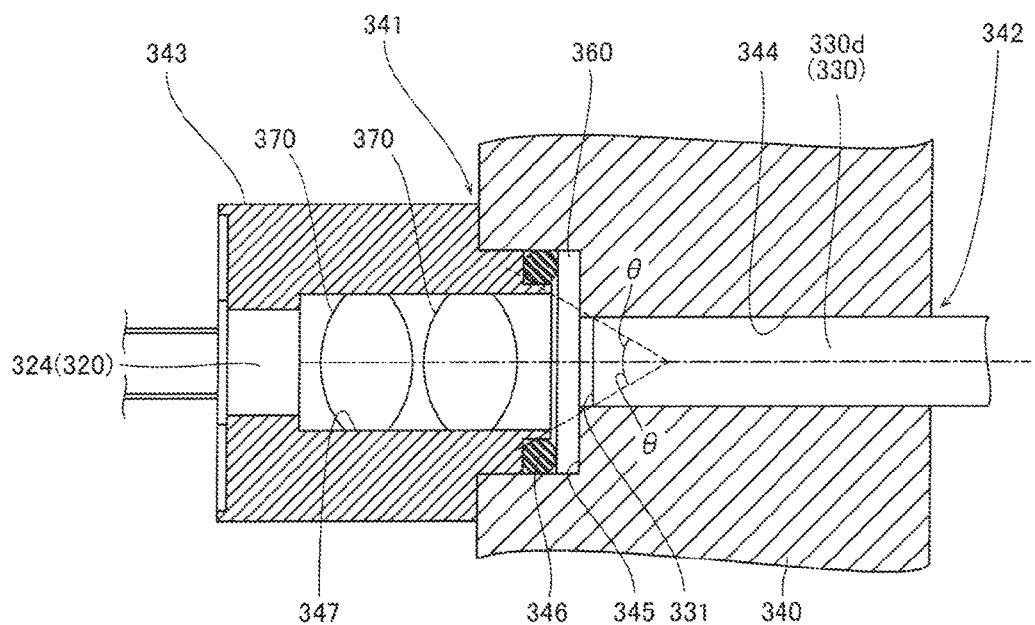
FIG. 6 is an enlarged cross-sectional view illustrating a configuration example of a holder for a fourth light source in FIG. 3.

Homogenization members 350 are disposed at two respective ejection ports 311 provided in housing 310. Each of homogenization members 350 has its incident plane 351 facing the corresponding one of exit ends 332 of optical fiber parts 330, and has its exit plane 352 disposed at the exit side of ejection port 311. Thus, light passing through homogenization member 350 and having its intensity distribution homogenized is emitted from each ejection port 311. Homogenization member 350 is configured to multiple-reflect the light entering from incident plane 351 therein and to emit the multiple-reflected light from exit plane 352. FIG. 6 illustrates light pipe 353 including a homogenizer rod having a polygonal columnar shape, as an example of homogenization member 350. Light pipe 353 multiple-reflects incident light therein, thereby emitting light having various wavelengths with a homogenized intensity distribution from exit plane 352. Note that, when the intensity distribution of the light having various wavelengths is sufficiently homogenized at exit ends 332 of optical fiber parts 330, no homogenization members 350 may be provided.

<Holding Member>

Referring back to FIG. 3, holding member 340 in light irradiation unit 10 holds five light sources 320. Therefore, five light sources 320 are supported by common holding member 340. Holding member 340 is made of metal such as aluminum, for example, and is formed into a prismatic shape. In the configuration example of FIG. 3, light source holder 341 and incident end holder 342 are provided at one end portion and the other end portion of holding member 340, respectively. Light source holder 341 and incident end holder 342 are connected to each other by passage section 344 including a through-hole that penetrates holding member 340.

Five light source holders 341 are linearly arranged along a direction orthogonal to a light emitting direction of each light source 320. As for light sources 320, fourth light source 324 is disposed in the center, fifth and second light sources 325 and 322 are disposed on either side of fourth light source 324, and first and third light sources 321 and 323 are disposed on the outermost side.

In the configuration example of FIG. 3, light source holders 341 that hold respective light sources 320 and incident end holders 342 that hold incident ends 331 of optical fiber parts 330 are disposed at positions linearly facing each other in holding member 340. Such a configuration allows optical axes of light sources 320 and axial centers of optical fiber parts 330 at incident ends 331 to easily and accurately coincide with each other. In FIG. 3, light source holders 341 and incident end holders 342 are disposed at positions facing each other on approximately the same axis line.

Figure 7:
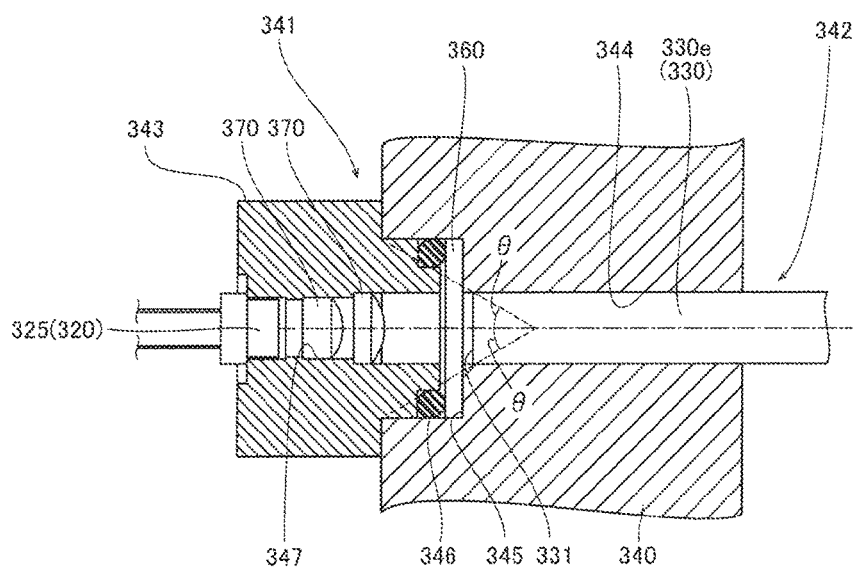
FIG. 7 is an enlarged cross-sectional view illustrating a configuration example of a holder for a fifth light source in FIG. 3.

In the configuration example of FIG. 3, each light source holder 341 holds light source 320 with socket 343, as illustrated in detail in FIGS. 6 and 7. Light source holder 341 includes concave section 345 connected to passage section 344, and socket 343 is a cylindrical member fitted to concave section 345. Light source 320 is held in a fixed state inside socket 343. Incident end holder 342 includes the other end portion of passage section 344 including the through-hole that penetrates holding member 340. Therefore, incident end holder 342 is a hole into which incident end 331 can be inserted, and holds a range of a predetermined length including incident end 331 of optical fiber part 330 by having the range inserted therein.

Light irradiation unit 10 may be provided with a member for collecting light from light source 320 on incident end 331 of optical fiber part 330. Light irradiation unit 10 may be provided with a member for controlling spectrum characteristics such as the center wavelength and a half width of light entering incident end 331.

<Optical Bandpass Filter>

In FIG. 3, for example, light irradiation unit 10 further includes optical bandpass filter 360 that transmits only light in a predetermined wavelength band. Optical bandpass filter 360 has a disk shape, and transmits only light in a predetermined wavelength band, among light applied onto one surface thereof, to the other surface thereof. Holding member 340 holds optical bandpass filter 360 at a position between light source 320 and incident end 331 of corresponding optical fiber part 330. Thus, light emitted from light source 320 can be made incident onto incident end 331 after adjusting the center wavelength, the half width, and the like of the light so as to obtain characteristics suitable for measurement. As a result, measurement accuracy is improved. Moreover, there is a case where there are individual differences among light sources 320, and the center wavelength, the half width, and the like differ thereamong. Even in such a case, a stable measurement result can be ensured by optical bandpass filter 360 absorbing the influence of the individual differences among light sources 320.

Figure 5:
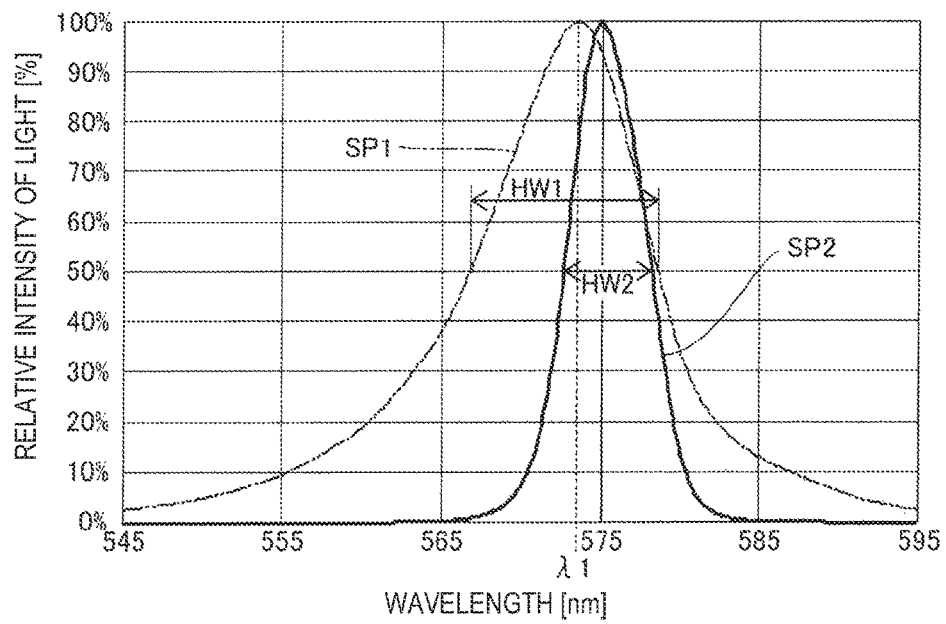
FIG. 5 is a diagram for explaining characteristics of an optical bandpass filter.

To be more specific, as illustrated in FIG. 5, it is assumed that fifth light source 325 that generates light having the fifth wavelength of 575 nm, for example, emits light with spectrum SP1 having a center wavelength λ1 and half width HW1, which is slightly shifted from 575 nm, to be exact. The light from fifth light source 325 coincides with the fifth wavelength of 575 nm by passing through optical bandpass filter 360, resulting in spectrum SP2 having sufficiently narrow half width HW2, and enters optical fiber part 330. Note that the vertical axis in FIG. 5 represents a relative intensity [%]. More specifically, FIG. 5 illustrates intensity distributions assuming that the maximum intensity in each of spectrums SP1 and SP2 is 100%. This does not mean that the maximum intensity (100%) of spectrum SP1 and the maximum intensity (100%) of spectrum SP2 in FIG. 5 coincide with each other. The both spectrums take different values as the absolute value of light intensity.

In the configuration example of FIG. 3, optical bandpass filters 360 are provided for all of five light sources 320. The characteristics of respective optical bandpass filters 360 vary corresponding to light source 320.

As illustrated in FIGS. 6 and 7, holding member 340 includes linear passage section 344 for linearly arranging light source 320, optical bandpass filter 360, and incident end 331 of optical fiber part 330 corresponding to light source 320. Optical bandpass filter 360 is disposed to block passage section 344 between light source 320 and incident end 331. Thus, the light from light source 320 can surely pass through optical bandpass filter 360 and enter incident end 331. As a result, occurrence of optical loss can be suppressed even when optical bandpass filters 360 are provided.

To be more specific, passage section 344 is a hole linearly extending inside holding member 340 along the optical axis of light source 320. Light source holder 341 includes concave section 345 formed to have an inside diameter larger than that of passage section 344. Optical bandpass filter 360 is disposed at the end portion on incident end holder 342 side inside concave section 345. Optical bandpass filter 360 is pressed against the bottom surface of concave section 345 through ring-shaped elastic member 346 by a tip surface of socket 343. Thus, optical bandpass filter 360 is provided to close passage section 344 in which incident end 331 is disposed. Optical bandpass filter 360 is pressed and fixed by elastic member 346 with moderate external force that does not cause damage.

<Condenser Lens>

In the configuration example of FIGS. 6 and 7, light irradiation unit 10 further includes condenser lenses 370. Condenser lenses 370 are provided corresponding to at least one of light sources 320, and converge light emitted from light source 320 onto incident end 331. Holding member 340 holds condenser lenses 370 at a position between light source 320 and incident end 331 of corresponding optical fiber part 330. Thus, use efficiency of the light generated by light source 320 can be improved. Thus, sufficient light intensity can be ensured without increasing the amount of light generated by light source 320 or a current value to be supplied to light source 320.

Condenser lenses 370 may be provided for all of five light sources 320, but do not always have to be provided when sufficient light intensity can be obtained with a predetermined current value of a rated current or less. It is effective to provide condenser lenses 370 for a light source having a relatively small light intensity among light sources 320. In the case of LED light sources, LED light sources of 340 nm and 575 nm generate less light among those of 660 nm, 405 nm, 800 nm, 340 nm, and 575 nm. Therefore, condenser lenses 370 are provided for fourth light source 324 (see FIG. 6) and fifth light source (see FIG. 7), among five light sources 320 illustrated in FIG. 3, and are not provided for first light source 321, second light source 322, and third light source 323.

In the configuration example of FIGS. 6 and 7, holding member 340 includes linear passage section 347 for linearly arranging light source 320, condenser lenses 370, and incident end 331 of optical fiber part 330 corresponding to light source 320. Condenser lenses 370 are disposed to block passage section 347 between light source 320 and incident end 331. Thus, axial alignment among light source 320, condenser lenses 370, and incident end 331 of optical fiber part 330 can be easily performed. As a result, the use efficiency of light can be effectively increased.

To be more specific, socket 343 includes linear passage section 347 between light source 320 and incident end of optical fiber part 330. Condenser lenses 370 are fitted into passage section 347 and held in socket 343 so as to block passage section 347. In the configuration example of FIGS. 6 and 7, two condenser lenses 370 are linearly arranged. The light from light source 320 is converged twice by two condenser lenses 370 before entering incident end 331. Thus, light emitted from light source 320 having a wider range can enter incident end 331 without increasing the distance between light source 320 and incident end 331. Note that, in order to transmit light through optical fiber part 330, the light needs to enter incident end 331 at incidence angle θ that meets predetermined total internal reflection conditions. Condenser lens 370 is configured to collect light such that light from light source 320 enters incident end 331 within a range of incidence angle θ. Only one condenser lens 370 may be provided.

<Positional Relationship Among Units>

Referring back to FIG. 3, light source holders 341 are arranged at intervals. In the configuration example of FIG. 3, light source holders 341 are provided to be linearly arranged at approximately equal intervals in holding member 340. Light source holders 341 allow light sources 320 to be arranged spaced apart from each other. Also, in the configuration example of FIG. 3, first distance D1 between at least one of light sources 320 and incident end 331 of corresponding optical fiber part 330 is smaller than second distance D2 between adjacent light sources 320. Thus, light source 320 and incident end 331 of optical fiber part 330 can be disposed at close positions, which are separated by first distance D1. As a result, optical axis alignment between light source 320 and incident end 331 can be easily performed.

Note that, in the configuration example of FIG. 3, first distance D1 is smaller than second distance D2 for first light source 321, second light source 322, and third light source 323. As for fourth and fifth light sources 324 and 325 to which condenser lenses 370 are provided, first distance D3 is larger than D1. The distances have a relationship of D1<D3<D2.

Also, in the configuration example of FIG. 3, optical fiber parts 330 are gathered and bundled along optical fiber part 330d corresponding to fourth light source 324. Optical fiber part 330d corresponding to fourth light source 324 is configured to be shortest in length from incident end 331 to exit end 332 among optical fiber parts 330. Here, among light sources 320, fourth light source 324 including an LED light source of 340 nm generates a smallest amount of light. Hence, in this configuration, optical fiber part 330d corresponding to fourth light source 324 that generates the smallest amount of light has the smallest path length. Therefore, optical loss during passage through optical fiber part 330 can be reduced. As a result, a larger amount of light to be generated by fourth light source 324 that generates a small amount of light can be ensured.

The longer the path length for gathering along optical fiber part 330d, the longer the length between incident end 331 and exit end 332. Therefore, the farther away from fourth light source 324 in the center, the longer the length between incident end 331 and exit end 332. For this reason, in the configuration example of FIG. 3, the relationship of the length from incident end 331 to exit end 332 among optical fiber parts 330 is 330d<330e and 330b<330a and 330c.

(Another Configuration Example of Light Irradiation Unit)

Figure 8:
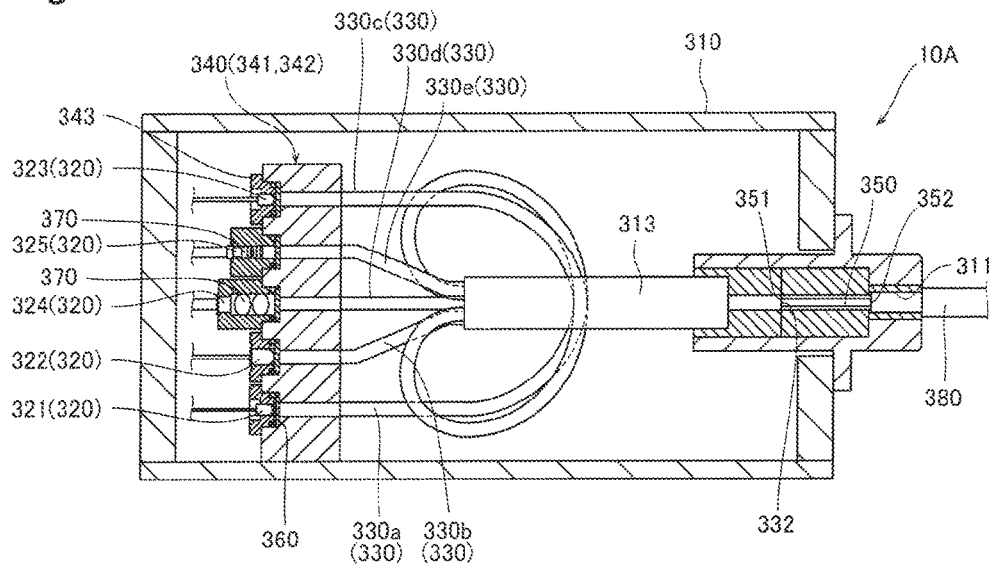
FIG. 8 is a schematic cross-sectional view illustrating another configuration example of the light irradiation unit.

FIG. 8 illustrates another configuration example of the light irradiation unit. In light irradiation unit 10A according to the configuration example of FIG. 8, housing 310 is provided with one ejection port 311. Light sources 320 are arranged in the same manner as the configuration example of FIG. 3, but may be arranged at different positions. Five optical fiber parts 330 are configured to be held by holding member 340 at positions where incident ends 331 and respective light sources 320 face each other, and to be twisted together in the middle and integrated to have one exit end 332. The twisted and integrated portion is housed in cylindrical holding member 313. At exit end 332, optical fibers included in optical fiber parts 330 are mixed in an approximately even distribution within an end surface of exit end 332.

The length between incident end 331 and exit end 332 is the smallest for optical fiber part 330d in the center corresponding to fourth light source 324. The farther away from optical fiber part 330d, the larger the length therebetween. For this reason, in the configuration example of FIG. 8, again, the relationship of the length from incident end 331 to exit end 332 among optical fiber parts 330 is 330d<330e and 330b<330a, 330c.

(Light Splitting Member and Detection Unit)

Next, description is given of a configuration for guiding light from light irradiation unit 10 to detection units 230 and 240 and a configuration of detection unit 230 (240). As described above, detection units 230 and 240 have the same configuration.

Figure 9:
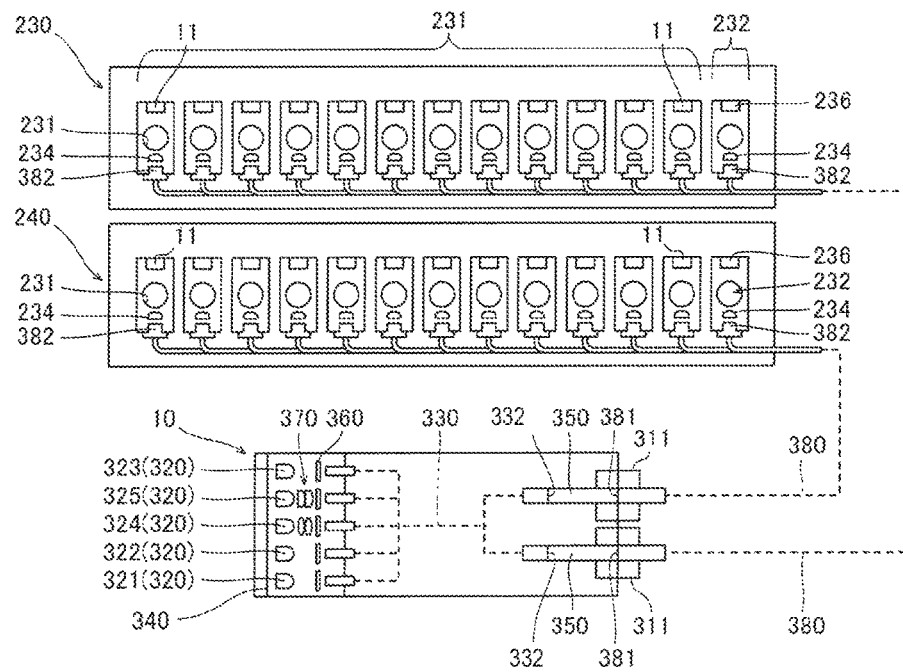
FIG. 9 is a schematic view illustrating a configuration for guiding light from the light irradiation unit to detection units.

In the configuration example of FIG. 9, light irradiation unit includes light splitting members 380 for splitting light from bundled exit end 332 to container installation sections 231. Light reception parts 11 are provided corresponding to container installation sections 231 and to detect light split to container installation sections 231 by light splitting members 380. Thus, measurement can be collectively performed by installing containers in container installation sections 231, respectively. Moreover, the light having the first to fifth wavelengths are evenly distributed at exit end 332. Thus, the light having the various wavelengths with a uniform intensity can be supplied in container installation sections 231 just by splitting the light from exit end 332 with light splitting members 380. As a result, light having a uniform intensity can be easily applied onto containers 15 without providing light sources 320 in respective container installation sections 231.

Two light splitting members 380 are provided corresponding to two detection units 230 and 240. In the configuration example of FIG. 9, each of detection units 230 and 240 includes twelve container installation sections 231 and one reference light measurement section 232. Twelve light reception parts 11 are provided in total for container installation sections 231, respectively. Moreover, reference light measurement section 232 is provided with reference light reception part 236. Reference light reception part 236 is provided in addition to light reception parts 11 and receives light from light irradiation unit 10 without transmitting the light through container 15. Light splitting members 380 split light to container installation sections 231 and reference light measurement sections 232 in detection units 230 and 240.

Each light splitting member 380 includes bundle of optical fibers similar to optical fiber part 330, for example. Incident ends 381 of light splitting members 380 are connected to ejection ports 311 provided in housing 310 of light irradiation unit 10, respectively. Incident ends 381 are arranged facing exit planes 352 of homogenization members 350. Thus, the light having the first to fifth wavelengths enter, with a homogenized light intensity, the individual optical fibers included in incident ends 381 of light splitting members 380. Exit ends 382 of light splitting members 380 are provided in the number equal to the total number of container installation sections 231 and reference light measurement sections 232. Exit ends 382 are connected to container installation sections 231 and reference light measurement sections 232, respectively. More specifically, in the configuration example of FIG. 9, each of light splitting members 380 includes thirteen branched exit ends 382.

Figure 10:
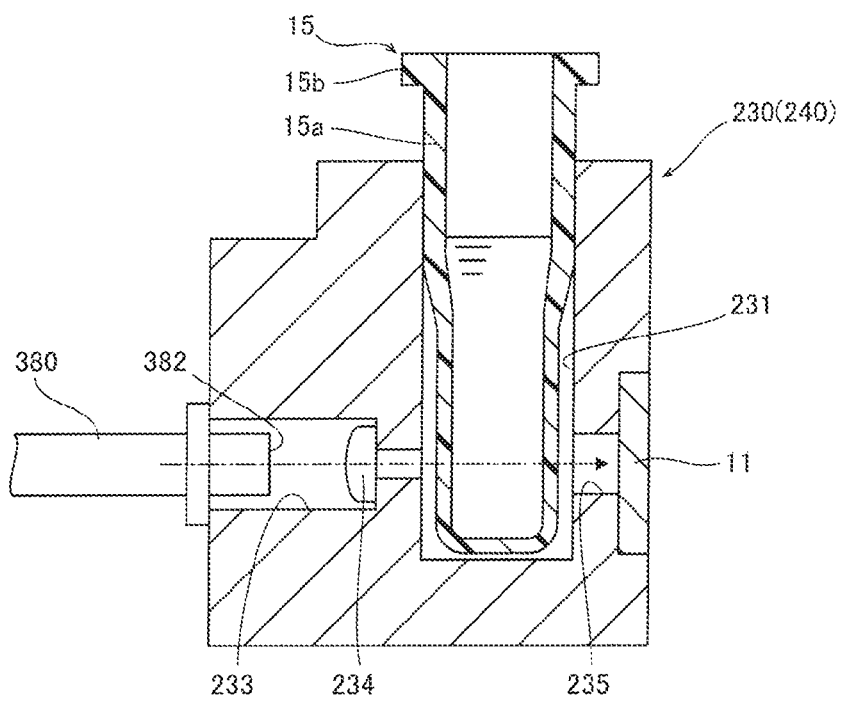
FIG. 10 is an enlarged cross-sectional view illustrating a configuration example of a container installation section in the detection unit.

FIG. 10 illustrates a configuration example of each of container installation sections 231. In the configuration example of FIG. 10, each of detection units 230 and 240 includes container installation section 231 as a vertically extending hole. Also, exit end 382 of light splitting member 380 is disposed in hole 233 laterally extending from container installation section 231. Condenser lens 234 is disposed in hole 233. Light reception part 11 is provided at an end portion of hole 235 formed opposite to hole 233 across container installation section 231. Thus, exit end 382 of light splitting member 380, condenser lens 234, container installation section 231, and light reception part 11 are linearly arranged. Light exiting from exit end 382 is transmitted through container 15 in container installation section 231 and a measurement specimen in container 15 after passing through condenser lens 234, and then detected by light reception part 11. Note that the measurement specimen is a liquid mixture of a sample and a reagent.

Container installation sections 231 and reference light measurement sections 232 have the same configuration. Each of reference light measurement sections 232 has no container 15 installed therein. Therefore, as for light split to reference light measurement section 232, the light from light irradiation unit 10 is received by reference light reception part 236 without being transmitted through container 15 and the measurement specimen. Light reception part 11 and reference light reception part 236 each output an electric signal depending on received light intensity.

(Controller)

Figure 11:
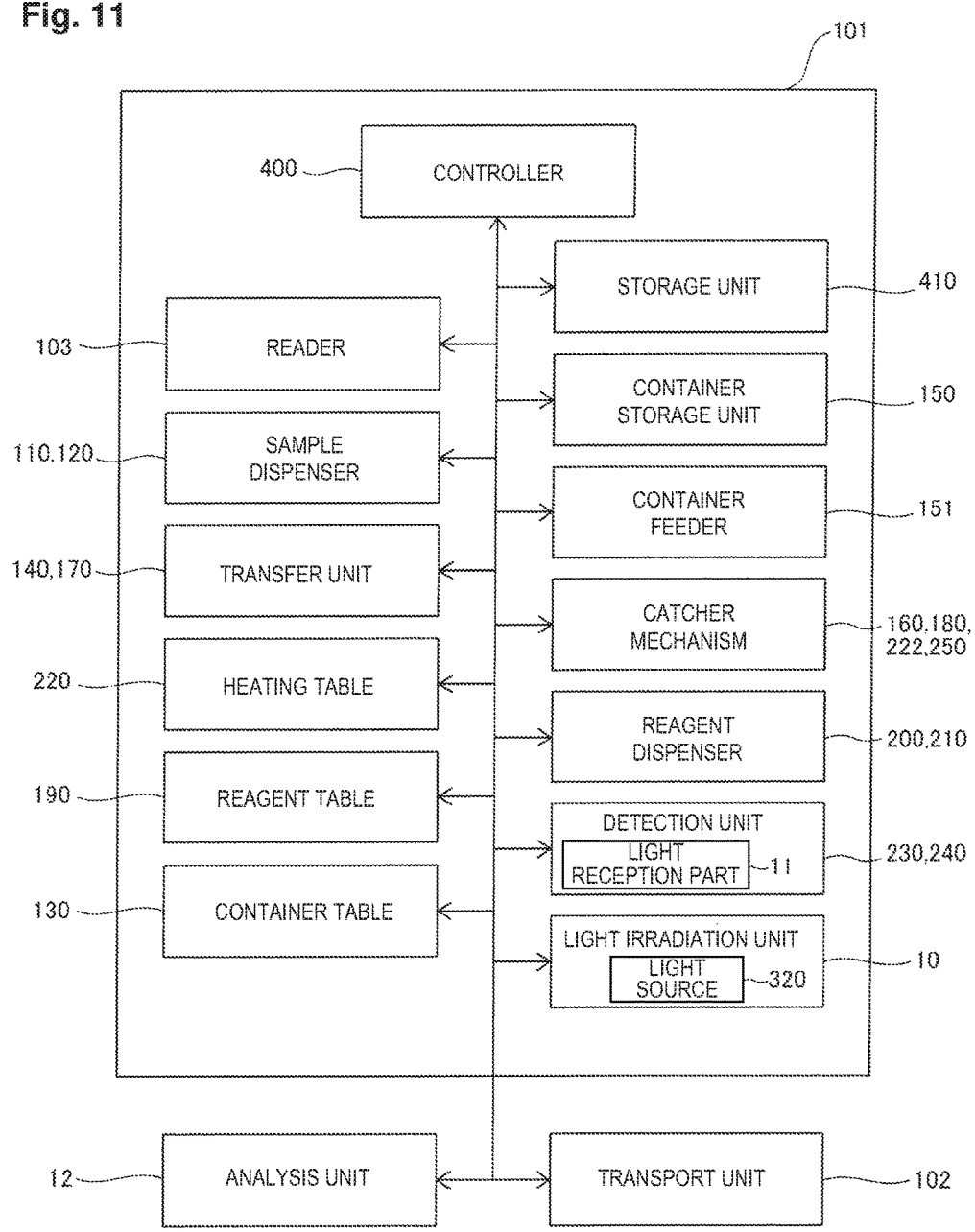
FIG. 11 is a block diagram illustrating a control configuration example of a measurement unit illustrated in FIG. 2.

As illustrated in FIG. 11, blood coagulation analyzer 100 includes controller 400 that controls operations of measurement unit 101. Controller 400 controls operations of light sources 320. Controller 400 includes an arithmetic processing unit such as a CPU (Central Processing Unit) or an FPGA (Field-Programmable Gate Array). Controller 400 controls units and parts in measurement unit 101 and transport unit 102 according to programs stored in storage unit 410. Storage unit 410 includes a storage medium such as a ROM (Read Only Memory), a RAM (Random Access Memory), and a hard disk, and stores programs and data required for operations of controller 400.

Figure 12:
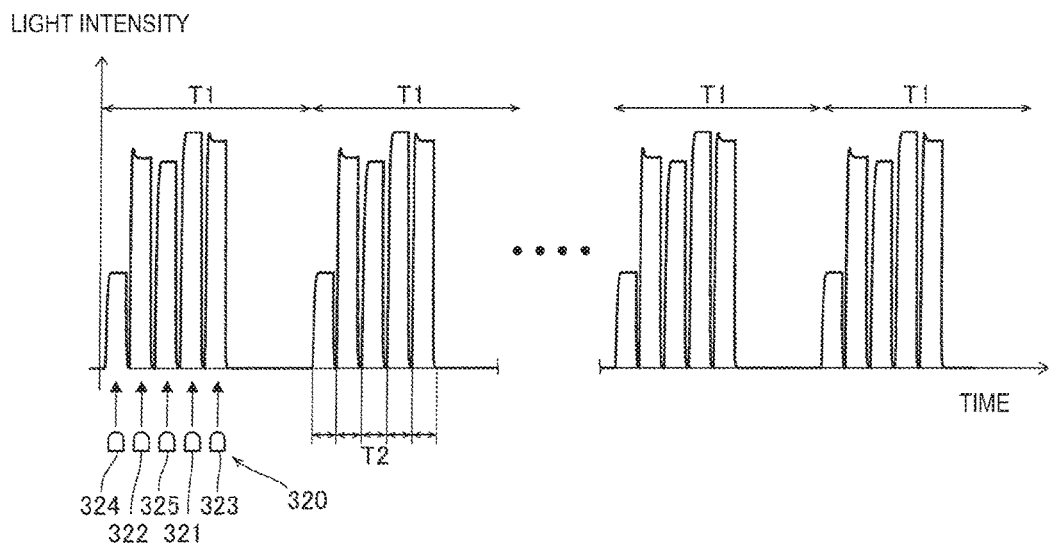
FIG. 12 is a diagram for explaining light emission control of each of the light sources by a controller.

In one configuration example, controller 400 sequentially controls light sources 320 one by one to periodically emit light. To be more specific, as illustrated in FIG. 12, controller 400 repeats control of sequentially causing five light sources 320 (first to fifth light sources 321 to 325) to emit light for predetermined light emission time T2 during light emission cycle T1. Light sources 320 are controlled to emit light in a pulse pattern of light emission time T2. Light reception part 11 and reference light reception part 236 individually acquire electric signals corresponding light from light sources 320, for each light emission cycle T1, in a temporally shifted manner. Such a configuration allows the light having the various wavelengths to be individually applied at the same light irradiation position. Therefore, even when the wavelength of light for use in measurement varies among samples, measurement can be performed at the same light irradiation position. Thus, the analyzer configuration can be simplified, unlike the case where, for example, light irradiation positions for specific wavelengths are provided corresponding to respective light sources 320.

Controller 400 performs light emission control for at least some of light sources 320 when a main power of analysis unit 12 and a main power of measurement unit 101 are turned on, for example. To be more specific, when the main power of analysis unit 12 and the main power of measurement unit 101 are turned on, controller 400 executes initial setting of measurement unit 101. Measurement unit 101 is set in a standby state upon completion of the initial setting of measurement unit 101. Controller 400 continues the control of sequentially causing light sources 320, one by one, to periodically emit light, at least until a shut-down instruction is received after measurement unit 101 is set in the standby state. Thus, a variation in light amount due to the influence of a temperature change immediately after the start of light emission and the like can be eliminated to make the light emission state stable during measurement. Controller 400 causes first light source 321, second light source 322, third light source 323, and fifth light source 325, for example, to emit light even in the standby state other than during a measurement operation.

Meanwhile, light sources 320 have different characteristics depending on the wavelength of light emitted. For example, the LED included in fourth light source 324 of 340 nm requires shorter time to make the light amount stable after the start of light emission control, compared with the other light sources. Therefore, controller 400 performs light emission control of some of light sources 320, for example, fourth light source 325 when the measurement operation is started, and causes fourth light source 324 to emit no light in the standby state other than during the measurement operation. Thus, the life of light sources 320 can be further extended.

In one configuration example, controller 400 is configured to control a current value to be supplied to each of light sources 320 in reference to an electric signal (hereinafter referred to as the reference signal) from reference light reception part 236. Thus, a change in light amount of light source 320 can be suppressed even when, for example, blood coagulation analyzer 100 is continuously operated over an extended time period. In the LED light source, for example, an element temperature change is likely to affect the amount of light emitted. Therefore, the light intensity of light source 320 can be maintained within an appropriate range that makes it possible to obtain a stable measurement result by controlling a current value so as to set the electric signal from reference light reception part 236 within a predetermined allowable range.

Figure 13:
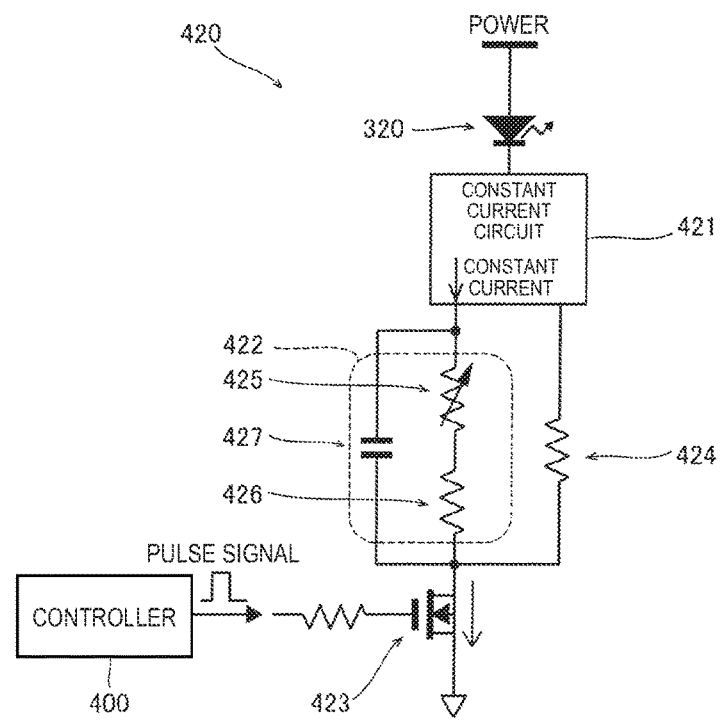
FIG. 13 is a diagram illustrating a configuration example of a drive circuit for the light source.

To be more specific, controller 400 controls drive circuit 420 for light source 320 illustrated in FIG. 13. FIG. 13 illustrates an example of a drive circuit for light emission control of one light source 320. Drive circuit 420 includes constant current circuit 421, RC circuit section 422, and switch section 423. Light source 320 and constant current circuit 421 are connected in series in this order to a power source. RC circuit section 422 and resistor 424 are connected in parallel to constant current circuit 421. Constant current circuit 421 supplies a predetermined constant current to RC circuit section 422. In constant current circuit 421, a current on resistor 424 side allows fluctuation. RC circuit section 422 is a parallel circuit in which variable resistor 425 and resistor 426 are connected in parallel with capacitor 427. RC circuit section 422 delays the rise of the current flowing through light source 320 according to a time constant proportional to the product of a combined resistance of variable resistor 425 and resistor 426 and a capacitance of capacitor 427. Thus, RC circuit section 422 suppresses large inrush currents flowing through light source 320 during switching.

RC circuit section 422 and resistor 424 are connected to switch section 423. Switch section 423 includes a transistor, and controls on and off of current supply to drive circuit 420 by voltage application to a gate.

Controller 400 controls individual light sources 320 to emit limit for predetermined light emission time T2 in predetermined light emission cycles T1 by applying a pulse signal to the gate of switch section 423. Since the current flowing through RC circuit section 422 is maintained constant by constant current circuit 421, the current value flowing on resistor 424 side is changed by changing a resistance value of variable resistor 425. The current value flowing through light source 320 is proportional to a ratio of resistance value R1 of RC circuit section 422 including variable resistor 425 and resistor 426 to resistance value R2 of resistor 424 (R1/R2). Controller 400 controls the current value to be supplied to light source 320 by changing the resistance value of variable resistor 425 in reference to the electric signal from reference light reception part 236.

Figure 14:
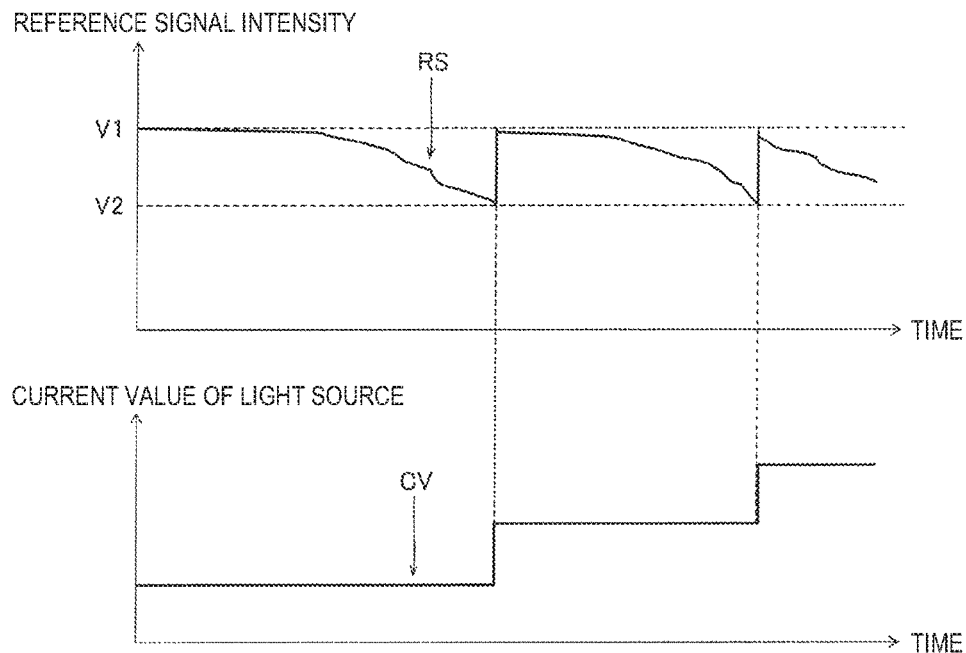
FIG. 14 is a diagram for explaining current value control of the light sources by the controller.

The current value control on light source 320 by controller 400 is performed in reference to reference value V1 and lower limit V2 of reference signal RS as illustrated in FIG. 14, for example. Controller 400 sets value CV of the current flowing to light source 320 so that reference signal RS is approximately equal to reference value V1 when the light emission control on light source 320 is started. The amount of light of the LED light source changes with an ambient temperature of the LED light source or a change in LED element over time. Therefore, when the amount of light of the light source 320 is reduced with the lapse of time, the intensity of reference signal RS is gradually lowered. Controller 400 performs control of correcting current value CV of light source 320 when the intensity of reference signal RS reaches lower limit V2. To be more specific, controller 400 calculates a current value after correction based on Formula (1) below.

Current value after correction = (reference value of reference signal/value at present of reference signal) × current value before correction (1)

Controller 400 corrects current value CV of light source 320 so as to obtain the calculated current value after correction by adjusting the resistance value of variable resistor 425. As a result, the amount of light of light source 320 reduced with time is increased every time reference signal RS reaches lower limit V2, and is maintained within an appropriate range between reference value V1 and lower limit V2.

(Analysis Unit)

Figure 15:
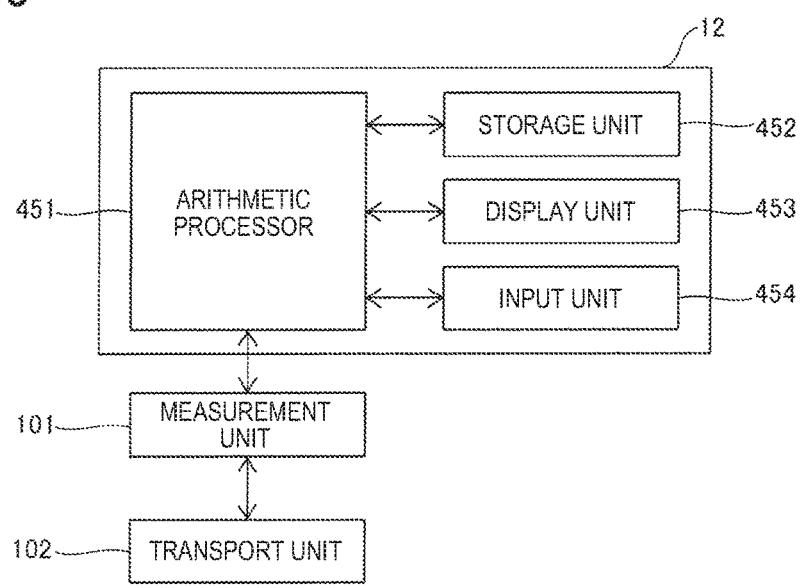
FIG. 15 is a block diagram illustrating a configuration example of an analysis unit.

In a configuration example illustrated in FIG. 15, analysis unit 12 includes arithmetic processor 451, storage unit 452, display unit 453, and input unit 454. Arithmetic processor 451 includes an arithmetic processing unit such as a CPU, and performs sample analysis processing according to a program stored in storage unit 452. Storage unit 452 includes a storage medium such as a ROM, a RAM, and a hard disk, and stores programs and data required for processing and control by arithmetic processor 451. Display unit 453 includes a display device such as a monitor. Input unit 454 includes an input device such as a keyboard and a mouse, and receives an operation input by the user. Analysis unit 12 includes a personal computer, for example.

Figure 16:
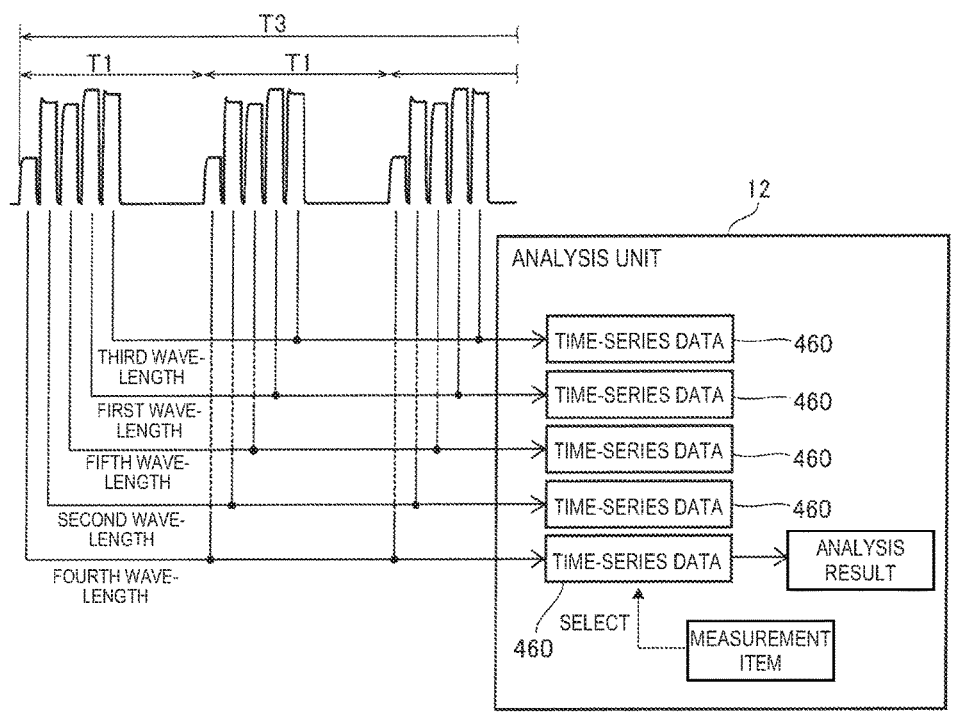
FIG. 16 is a conceptual diagram for explaining analysis processing by the analysis unit.

In a configuration example of FIG. 16, analysis unit 12 creates time-series data 460 corresponding to light sources 320 from electric signals outputted from light reception part 11 for a sample in container installed in container installation section 231. As described above, the light from five light sources 320 in light irradiation unit are sequentially supplied to container installation section 231 for each predetermined light emission cycle T1. Therefore, when container 15 is installed in container installation section 231, the light from five light sources 320 are transmitted through container and the measurement specimen, and sequentially detected by light reception part 11. As a result, five electric signals corresponding to the light having the first to fifth wavelengths, respectively, are outputted to controller 400 from light reception part 11 for each light emission cycle T1. Analysis unit 12 receives the electric signals from controller 400 and stores the received electric signals in storage unit 452.

During measurement time T3 for which container 15 is installed in container installation section 231, one piece of data is acquired in each light emission cycle T1 for each of the light beams having the first to fifth wavelengths. The five electric signals have the intensity reflecting the state of the measurement specimen irradiated with light. Each piece of time-series data 460 includes T3/T1 pieces of data, and is acquired for each wavelength. In the case of applying the light having the first to fifth wavelengths, five kinds of time-series data 460 are acquired.

Analysis unit 12 analyzes the sample by selecting the time-series data 460 corresponding to the measurement item from among the multiple pieces of time-series data 460. Such a configuration in which time-series data 460 is acquired for each wavelength and time-series data 460 to be used for analysis is selected can standardize the control regarding the acquisition of time-series data 460 regardless of the measurement item. For example, there is no need to perform such control as to read data from light reception part 11 in accordance with the timing of applying light having a specific wavelength during light emission cycle T1. Thus, the control regarding the acquisition of time-series data 460 can be simplified.

When the measurement item of the sample in container 15 installed in container installation section 231 is the one for blood coagulation measurement, analysis unit 12 calculates a coagulation time and a concentration or activity of components contained in the sample from time-series data 460 corresponding to the first wavelength. More specifically, analysis unit 12 selects time-series data 460 acquired using the electric signal of the light from first light source 321, and calculates a coagulation time based on a change in amount of light received in time-series data 460. Thus, the coagulation time can be acquired using the light from first light source 321 provided for coagulation time measurement. Therefore, an accurate and stable measurement result can be obtained.

Analysis unit 12 uses a percentage detection method, for example, to calculate the coagulation time. To be more specific, assuming that the received light intensity immediately after addition of a reagent is 0% and the received light intensity at the end of coagulation reaction is 100%, analysis unit 12 obtains a time when the received light intensity reaches a predetermined value set in advance from a reaction curve, and sets the time obtained as the coagulation time. Also, analysis unit 12 creates in advance a calibration curve associating the coagulation time with the activity or concentration of target components of the measurement item, and stores the calibration curve in storage unit 452. Thus, analysis unit 12 acquires the concentration or activity of the target components of the measurement item, using the calculated coagulation time and the calibration curve.

When the measurement item of the sample in container 15 installed in container installation section 231 is the one for synthetic substrate measurement, analysis unit 12 calculates a concentration or activity of components contained in the sample from time-series data 460 corresponding to the second wavelength. Therefore, the synthetic substrate measurement can be performed using the light from second light source 322 provided for synthetic substrate measurement. Thus, an accurate and stable measurement result can be obtained. In a configuration in which fourth light source 324 is provided in addition to second light source 322, analysis unit 12 calculates the concentration or activity of the components contained in the sample from time-series data 460 corresponding to the second wavelength and/or the fourth wavelength. Analysis unit 12 analyzes a process of coloring by a chromogenic synthetic substrate, using the electric signal corresponding to the second wavelength or the fourth wavelength outputted from light reception part 11. More specifically, analysis unit 12 selects time-series data 460 acquired using the electric signal of the light from second light source 322 or fourth light source 324, and analyzes a degree of coloring based on a change in amount of light received in time-series data 460.

In the synthetic substrate measurement, analysis unit 12 uses a Rate method or a Vlin method, for example, to obtain a change in absorbance. The Rate method is a method of analyzing a change in amount of light received during a time period between predetermined start point and end point in time-series data 460, and calculating a change in absorbance per unit time by linear regression. The Vlin method is a method of setting a start point and an end point in time-series data 460, at which a change in absorbance is maximized and linear approximation is optimized for each sample, analyzing a change in amount of light received during a time period between the set start point and end point, and calculating a change in absorbance per unit time by linear regression. Analysis unit 12 creates in advance a calibration curve associating the change in absorbance with the activity or concentration of target components of the measurement item, and stores the calibration curve in storage unit 452. Thus, analysis unit 12 acquires the concentration or activity of the target components of the measurement item, using the calculated change in absorbance and the calibration curve.

When the measurement item of the sample in container 15 installed in container installation section 231 is the one for immunonephelometry measurement, analysis unit 12 calculates a concentration or activity of components contained in the sample from time-series data 460 corresponding to the third wavelength. Therefore, the immunonephelometry measurement can be performed using the light from third light source 323 provided for immunonephelometry measurement. Thus, an accurate and stable measurement result can be obtained. In a configuration in which fifth light source 325 is provided in addition to third light source 323, analysis unit 12 calculates the concentration or activity of the components contained in the sample from time-series data 460 corresponding to the third wavelength and/or the fifth wavelength. Analysis unit 12 analyzes a process of antigen-antibody reaction between the sample and an antibody sensitizing reagent, using the electric signal corresponding to the third wavelength or the fifth wavelength outputted from light reception part 11. More specifically, analysis unit 12 selects time-series data 460 acquired using the electric signal of the light from third light source 323 or fifth light source 325, and analyzes an agglutination rate by the antigen-antibody reaction based on a change in amount of light received in time-series data 460.

In the immunonephelometry measurement, analysis unit 12 uses the Rate method or the Vlin method, for example, to obtain a change in absorbance, as in the case of the synthetic substrate measurement. Analysis unit 12 creates in advance a calibration curve associating the change in absorbance with the activity or concentration of target components of the measurement item, and stores the calibration curve in storage unit 452. Thus, analysis unit 12 acquires the concentration or activity of the target components of the measurement item, using the calculated change in absorbance and the calibration curve.

Note that, when light reception part 11 receives transmitted light of the light applied onto the measurement specimen, the received light intensity is at its maximum immediately after the addition of the reagent, and is reduced with the lapse of time. On the other hand, when light reception part 11 receives scattered light of the light applied onto the measurement specimen, the received light intensity is at its minimum immediately after the addition of the reagent, and is increased with the lapse of time. A direction of increase or decrease in received light intensity with the lapse of time differs between the transmitted light and the scattered light. However, it is common between the transmitted light and the scattered light that the coagulation time or the change in absorbance is calculated and the analysis of the measurement item is performed using the calibration curve.

(Measurement Operation of Blood Coagulation Analyzer)

Figure 17:
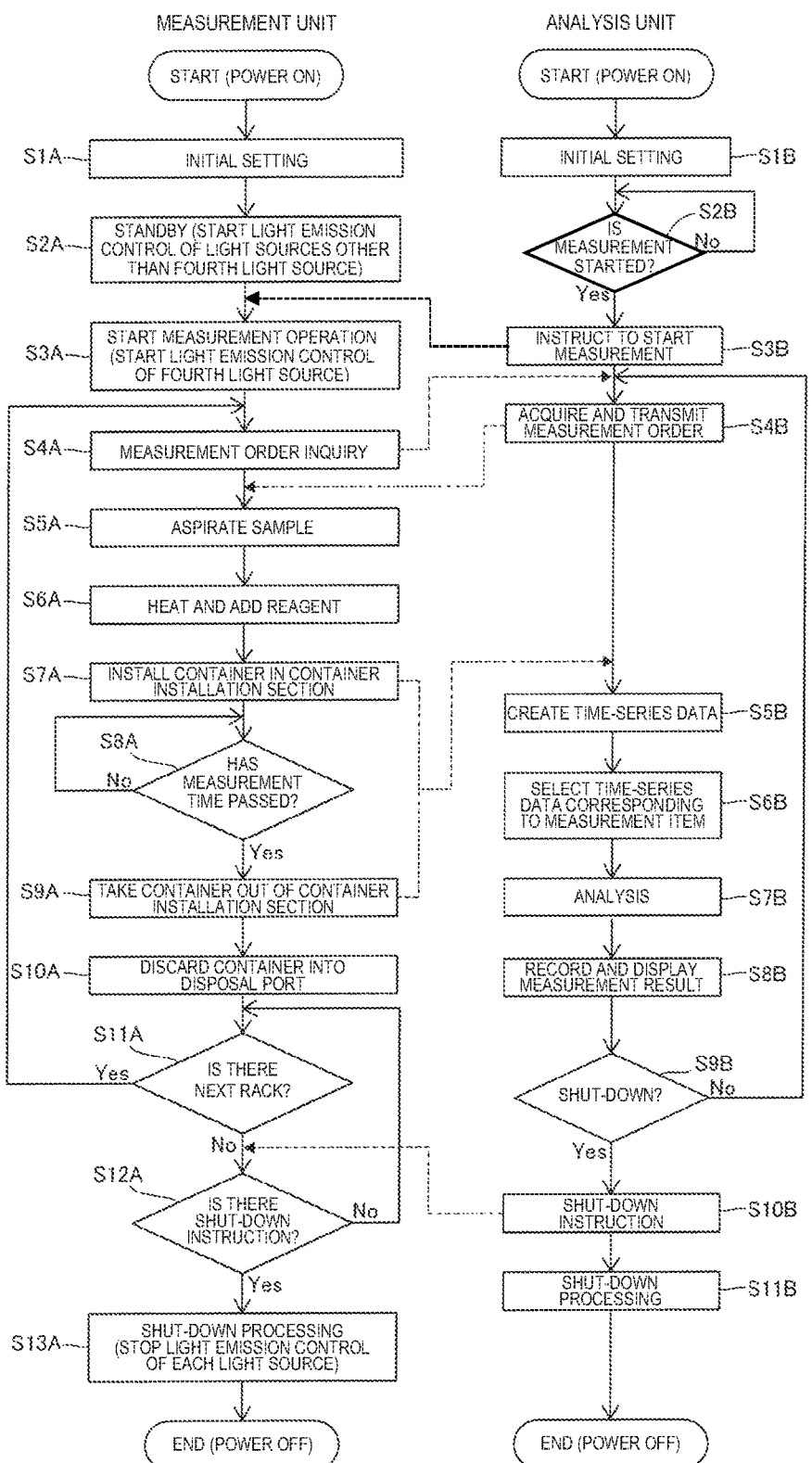
FIG. 17 is a flowchart for explaining operations of the blood coagulation analyzer illustrated in FIG. 2.
Figure 18:
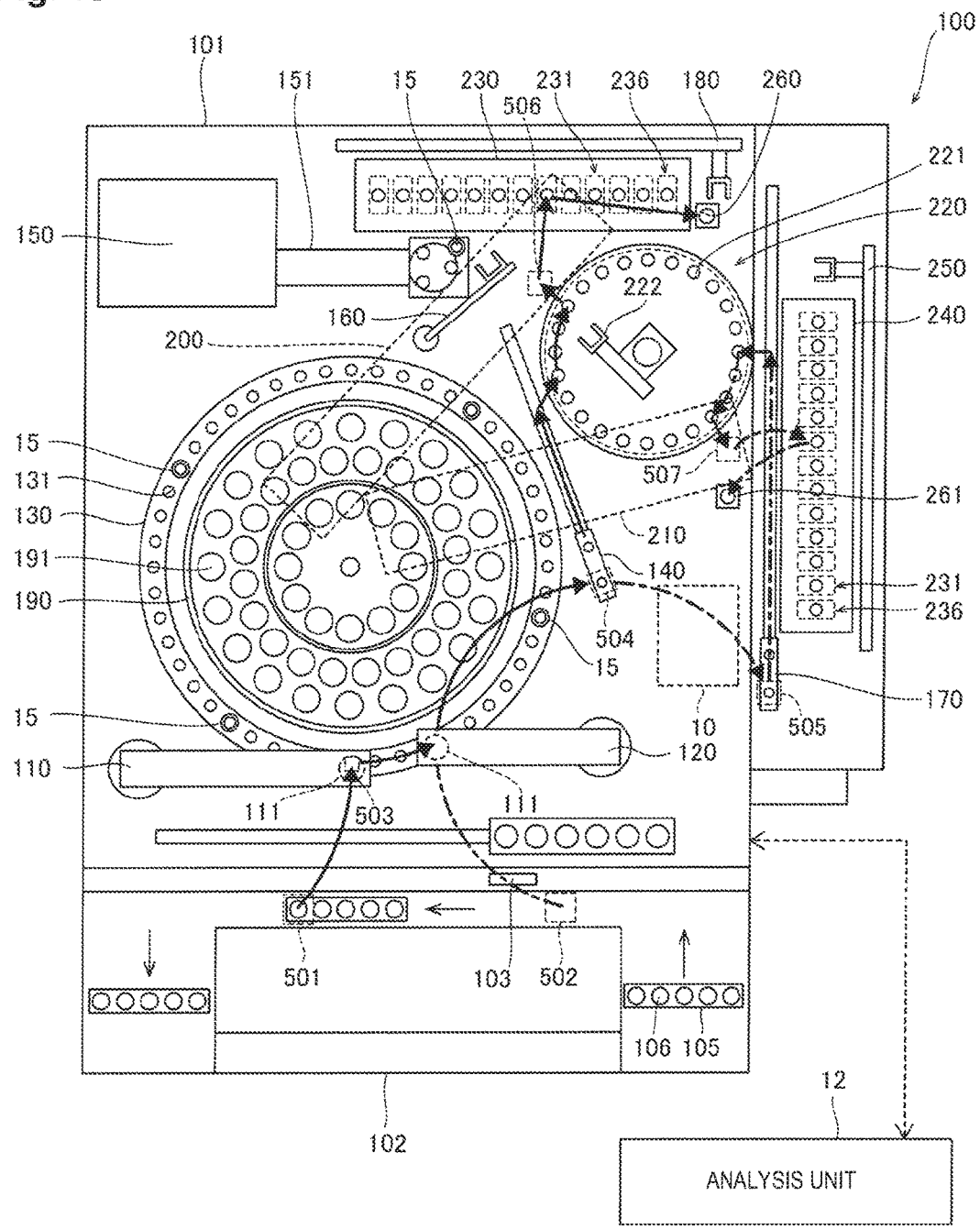
FIG. 18 is a diagram for explaining operations of the blood coagulation analyzer illustrated in FIG. 2.

With reference to FIGS. 17 and 18, description is given of a measurement operation performed by blood coagulation analyzer 100 in the configuration example of FIG. 2. Controller 400 performs operation control of measurement unit 101 and transport unit 102. Arithmetic processor 451 performs control of analysis unit 12. Hereinafter, FIG. 18 is referred to for the units in measurement unit 101 and transport unit 102.

When a main power of analysis unit 12 and a main power of measurement unit 101 are turned on by the user, a control operation of FIG. 17 is started. In Step S1A, controller 400 performs initial setting such as initialization processing of measurement unit 101. Meanwhile, in Step S1B, arithmetic processor 451 performs initial setting such as initialization processing of analysis unit 12.

After the completion of the initial setting, controller 400 shifts to a standby state in Step S2A. After shifting to the standby state, controller 400 starts light emission control of sequentially causing first light source 321, second light source 322, third light source 323, and fifth light source 325 except for fourth light source 324, one by one, to periodically emit light. The light emission control is continued until a shut-down instruction to be described later is received.

In the standby state, controller 400 waits for a measurement start instruction from analysis unit 12. In Step S2B, arithmetic processor 451 determines whether to start measurement. Arithmetic processor 451 stands by while repeating Step S2B until an operation input to start measurement by the user using input unit 454 is received. Upon receipt of the input operation to start measurement by the user, arithmetic processor 451 transmits an instruction to start measurement to controller 400 in Step S3B.

Upon receipt of the instruction to start measurement from analysis unit 12, controller 400 starts a measurement operation in Step S3A. At the timing of starting the measurement operation, controller 400 starts light emission control of fourth light source 324. Thus, five light sources 320 are sequentially controlled one by one to periodically emit light. Moreover, controller 400 controls transport unit 102 to transport sample rack 105 so that sample container 106 to be aspirated is disposed at a sample aspirating position. During the transportation of sample rack 105, reader 103 reads identification information on sample rack 105 and sample container 106.

In Step S4A, controller 400 transmits a measurement order inquiry including the read-out identification information to analysis unit 12. Upon receipt of the measurement order inquiry, arithmetic processor 451 acquires a measurement order of a sample corresponding to the identification information, and transmits the acquired measurement order to controller 400. The measurement order is recorded, in association with the identification information on the sample, in storage unit 452 or an external host computer connected to analysis unit 12.

Upon receipt of the measurement order, controller 400 causes sample dispenser 110 or 120 to aspirate the sample and dispense the sample into new container 15 in Step S5A. Then, in Step S6A, controller 400 controls measurement unit 101 to heat container 15 with heating table 220 and to add a reagent into container 15 with reagent dispenser 200 or 210. Thus, a measurement specimen containing the sample and the reagent is prepared in container 15. In Step S7A, controller 400 controls measurement unit 101 to install container 15 storing the measurement specimen in container installation section 231 in detection unit 230 or 240. Note that operations of measurement unit 101 in Steps S5A to S10A are described in detail later.

Once the measurement operation is started in Step S3A, light having first to fifth wavelengths from light irradiation unit 10 are sequentially applied onto each container installation section 231. With the installation of container 15 in container installation section 231, the light from light irradiation unit 10 is applied onto container 15, and light reception part 11 receiving light transmitted through container 15 outputs an electric signal. The electric signal is transmitted to analysis unit 12 through controller 400.

In Step S8A, controller 400 determines whether or not predetermined measurement time T3 corresponding to a measurement item specified in the measurement order has passed since the installation of container 15 in container installation section 231. The acquisition of the electric signal and the transmission thereof to analysis unit 12 are carried on during predetermined measurement time T3. In Step S5B, arithmetic processor 451 in analysis unit 12 generates five kinds of time-series data 460 for the respective wavelengths of the light, from the electric signals for the wavelengths received during measurement time T3.

Note that the length of measurement time T3 differs among the measurement items as described above. As an example, measurement time T3 is 170 seconds for PT and APTT as the measurement item for blood coagulation measurement, and measurement time T3 is 100 seconds for Fbg as the measurement item for blood coagulation measurement. For ATIII as the measurement item for synthetic substrate measurement, measurement time T3 is 60 seconds. For D-dimer as the measurement item for immunonephelometry measurement, measurement time T3 is 200 seconds.

After the elapse of measurement time T3 in Step S8A, controller 400 moves to Step S9A to take container 15 out of container installation section 231, and then discards container 15 taken out through disposal port 260 or 261 in Step S10A. Catcher mechanism 180 or 250 transfers container 15.

In Steps S7A to S10A, as described above, controller 400 installs container 15 storing the measurement specimen in container installation section 231, takes container 15 out of container installation section 231 after the elapse of measurement time T3 corresponding to the measurement item for the sample in container 15 installed in container installation section 231, and then controls catcher mechanism 180 or 250 to discard container 15 through disposal port 260 or 261. Thus, measurements corresponding to various measurement items can be performed with the same analyzer configuration only by changing the installation time of container 15 in container installation section 231.

Meanwhile, in analysis unit 12, arithmetic processor 451 selects time-series data 460 corresponding to the measurement item, from among five kinds of time-series data 460 created, in Step S6B. In Step S7B, arithmetic processor 451 uses time-series data 460 selected to perform analysis and generate a measurement result. In Step S8B, arithmetic processor 451 performs recording of the obtained measurement result in storage unit 452, display of the measurement result on display unit 453, and the like.

In Step S11A, controller 400 determines whether or not there is next sample rack 105 in transport unit 102. When there is next sample rack 105, controller 400 returns to Step S4A to continue the measurement operation. When there is no next sample rack 105, controller 400 determines whether or not a shut-down instruction is received from analysis unit 12 in Step S12A, and shifts to the standby state.

Meanwhile, in Step S9B, arithmetic processor 451 determines whether to perform shut-down processing. When not performing the shut-down processing, arithmetic processor 451 continues the analysis operation from Step S4B to Step S8B with the electric signal transmitted along with the measurement operation by measurement unit 101. Upon receipt of a shut-down input operation from the user, arithmetic processor 451 transmits a shut-down instruction to controller 400 in Step S10B.

Upon receipt of the shut-down instruction from analysis unit 12, controller 400 moves to Step S13A to perform predetermined shut-down processing. In the shut-down processing, controller 400 stops the light emission control of light sources 320. Thus, the application of light from light irradiation unit 10 is stopped.

Controller 400 turns off the power of measurement unit 101 after the shut-down processing in Step S13A. Meanwhile, arithmetic processor 451 terminates the processing and turns off the power of analysis unit 12 after the shut-down processing in Step S11B.

(Measurement Operation of Measurement Unit)

Next, detailed description is given of the operations of measurement unit 101 in Steps S5A to S10A. As illustrated in FIG. 18, the operations of measurement unit 101 differ between a case where measurement is performed by transferring container 15 to detection unit 230 and a case where measurement is performed by transferring container 15 to detection unit 240. Thus, description is given of both cases.

<Measurement with Detection Unit 230>

In the case of measurement of the sample using detection unit 230, sample dispenser 110 aspirates the sample from sample container 106 at sample aspirating position 501. Sample dispenser 110 dispenses the sample into container 15 held on container table 130. Container table 130 is rotated in the circumferential direction to transfer container 15 to a position where the sample can be aspirated by sample dispenser 120. Then, sample dispenser 120 aspirates the sample in container 15, and dispenses the sample into container 15 held by transfer unit 140 at sample dispensing position 503 on container table 130. Transfer unit 140 is moved to the vicinity of heating table 220, and catcher mechanism 222 takes out container 15 on transfer unit 140 and installs container 15 on heating table 220. If necessary, catcher mechanism 222 transfers container 15 to reagent dispensing position 506, and reagent dispenser 200 dispenses an adjusted reagent into container 15. After the dispensing, catcher mechanism 222 returns container 15 to heating table 220.

After the completion of the heating with heating table 220, container 15 transferred to a predetermined ejection position by heating table 220 is taken out by catcher mechanism 180 and transferred to reagent dispensing position 506. Then, reagent dispenser 200 dispenses the reagent into container 15. After dispensing the reagent, catcher mechanism 180 installs container 15 into any of container installation sections 231 in detection unit 230. With the installation of container 15 in container installation section 231, the light from light irradiation unit 10 is applied onto container 15. Light reception part 11 receives the light transmitted through container 15 and the measurement specimen, and outputs an electric signal. The electric signal is transmitted to analysis unit 12 through controller 400. The acquisition of the electric signal is carried on during measurement time T3, and analysis unit 12 crates time-series data 460 for each wavelength of the light. After the elapse of measurement time T3, catcher mechanism 180 takes container 15 out of container installation section 231 and transfers container 15 to disposal port 260. Analysis unit 12 selects time-series data 460 corresponding to the measurement item, and analyzes time-series data 460 selected. Then, analysis unit 12 displays an analysis result on display unit 453 and records the analysis result in storage unit 452.

<Measurement with Detection Unit 240>

In the case of measurement of the sample using detection unit 240, sample dispenser 110 aspirates the sample from sample container 106 at sample aspirating position 501. Sample dispenser 110 dispenses the sample into container 15 held on container table 130. Container table 130 is rotated in the circumferential direction to transfer container 15 to a position where the sample can be aspirated by sample dispenser 120. Then, sample dispenser 120 aspirates the sample in container 15, and dispenses the sample into container 15 held by transfer unit 170 at sample dispensing position 504. Transfer unit 170 is moved to the vicinity of heating table 220, and catcher mechanism 222 takes out container 15 on transfer unit 170 and installs container on heating table 220. If necessary, catcher mechanism 222 transfers container 15 to reagent dispensing position 507, and reagent dispenser 210 dispenses an adjusted reagent into container 15. After the dispensing, catcher mechanism 222 returns container 15 to heating table 220.

After the completion of the heating with heating table 220, container 15 transferred to a predetermined ejection position by heating table 220 is taken out by catcher mechanism 250 and transferred to reagent dispensing position 507. Then, reagent dispenser 210 dispenses the reagent into container 15. After dispensing the reagent, catcher mechanism 250 installs container 15 into any of container installation sections 231 in detection unit 240. A measurement operation with detection unit 240 is similar to that with detection unit 230. After the elapse of a predetermined measurement time, catcher mechanism 250 takes container 15 out of container installation section 231 and transfers container 15 to disposal port 261. The operation of analysis unit 12 with detection unit 240 is performed in the same way as with detection unit 230.

Note that sample dispenser 120 can also aspirate the sample from sample container 106 at sample aspirating position 502 and dispense the sample directly into container 15 transferred to sample dispensing position 504 or 505. When the sample is dispensed into container 15 at sample dispensing position 504, measurement is performed with detection unit 230. On the other hand, when the sample is dispensed into container 15 at sample dispensing position 505, measurement is performed with detection unit 240. The operations after the dispensing are as described above.

The blood coagulation analyzer of Patent Document 1 described above is provided with the halogen lamp, which is larger in size than a semiconductor light emitting element such as an LED, and the filter unit provided with a rotation mechanism. Therefore, the analyzer configuration is increased in size. Also, the life of the halogen lamp is short.

To solve such a problem, the analyzer may simply employ a configuration in which LEDs having a longer life than the halogen lamp are used and light from each of the LEDs is made incident onto an optical fiber coupler with mirrors and a dichroic mirror. In this case, however, precise work is required for optical axis alignment to make the optical axes of the light sources coincide with each other. Therefore, a blood coagulation analyzer which applies light having different wavelengths for blood coagulation analysis is desired to have a configuration that makes it possible to suppress an increase in size of the analyzer configuration, to extend the life of a light source, and to easily suppress the occurrence of optical axis misalignment.

According to the embodiments described above, a blood coagulation analyzer which applies light having different wavelengths for blood coagulation analysis makes it possible to suppress an increase in size of the analyzer configuration. Also, the life of a light source can be extended, and the occurrence of optical axis misalignment can be easily suppressed.

Note that the embodiment disclosed herein should be considered in all respects to be illustrative and not restrictive. The scope of the invention is defined by the scope of claims rather than the above description of the embodiment, and includes all modifications within the scope and meanings equivalent to those of the claims.

What is claimed is:

1. A blood coagulation analyzer comprising:
   a light irradiation unit configured to apply light onto a container configured to store a measurement specimen containing a sample and a reagent, and comprising:
      light sources including a first light source configured to generate light of a first wavelength for blood coagulation time measurement, a second light source configured to generate light of a second wavelength for synthetic substrate measurement, and a third light source configured to generate light of a third wavelength for immunonephelometry measurement; and
      optical fiber parts facing the respective light sources;
   a light reception part configured to receive light transmitted through the container;
   an analysis unit configured to analyze the sample using an electric signal outputted from the light reception part;
   light source holders holding the respective light sources; and
   incident end holders holding incident ends of the optical fiber parts such that the incident ends face the respective light sources.

2. The blood coagulation analyzer according to claim 1, further comprising:
   a holding member including the light source holders and the incident end holders.

3. The blood coagulation analyzer according to claim 1, wherein
   each of the optical fiber parts comprises optical fibers, and
   the optical fibers for the different light sources are mixed in an approximately even distribution at each exit end of the optical fiber parts.

4. The blood coagulation analyzer according to claim 3, further comprising:
   container installation sections at each of which the container is to be installed, wherein
   the light irradiation unit further comprises a light splitting member configured to split light from the exit end to the container installation sections, and
   the light reception parts are provided corresponding to the container installation sections and configured to detect light split to the container installation sections by the light splitting member.

5. The blood coagulation analyzer according to claim 1, further comprising:
   detection units each including container installation sections, wherein
   each of the optical fiber parts comprises optical fibers, an incident end and an exit end
   the optical fiber parts are bundled such that the optical fibers for the different light sources are mixed in an approximately even distribution at a position between the incident ends and the exit ends, and
   the optical fiber parts are divided into branches corresponding to the detection units such that the optical fibers for the different light sources are mixed and distributed approximately evenly at the exit ends.

6. The blood coagulation analyzer according to claim 3, wherein
   the light irradiation unit further comprises a homogenization member adjacent to the exit end and configured to homogenize an intensity distribution of light incident from the exit end and to output the resultant light.

7. The blood coagulation analyzer according to claim 2, wherein each of the light source holders and a corresponding one of the incident end holders linearly face each other in the holding member.

8. The blood coagulation analyzer according to claim 2, wherein
the light irradiation unit further comprises optical bandpass filters each of which is configured to transmit light in a predetermined wavelength band, and
the holding member holds the optical bandpass filters, respectively, between the light sources and the incident ends of the corresponding optical fiber members.

9. The blood coagulation analyzer according to claim 8, wherein
the holding member includes a linear passage section in which each of the light sources, the corresponding optical bandpass filter, and the incident end of the optical fiber part corresponding to the light source are linearly arranged, and
the optical bandpass filter is provided so as to block the passage section between the light source and the incident end.

10. The blood coagulation analyzer according to claim 2, wherein
the light irradiation unit further comprises a condenser lens which is provided corresponding to at least one of the light sources, and which converges light emitted from the light source onto the incident end, wherein
the holding member holds the condenser lens at a position between the light source and the incident end of the corresponding optical fiber part.

11. The blood coagulation analyzer according to claim 10, wherein
the holding member includes a linear passage section in which the light source, the condenser lens, and the incident end of the optical fiber part corresponding to the light source are linearly arranged, and
the condenser lens is provided so as to block the passage section between the light source and the incident end.

12. The blood coagulation analyzer according to claim 1, wherein
the light sources are arranged apart from each other, and
a first distance between at least one of the light sources and the incident end of the corresponding optical fiber part is smaller than a second distance between the light sources adjacent to each other.

13. The blood coagulation analyzer according to claim 1, further comprising:
a controller configured to control operations of the light sources, wherein
the controller sequentially controls the light sources, one by one, to periodically emit light.

14. The blood coagulation analyzer according to claim 13, wherein
the analysis unit configured to create time-series data corresponding to the light sources from detection signals outputted from the light reception part for the sample in the container installed in the container installation section, and
the analysis unit configured to analyze the sample by selecting the time-series data suited to a measurement item from among the created time-series data.

15. The blood coagulation analyzer according to claim 1, further comprising:
container installation sections at each of which the container is to be installed; and
a controller configured to control operations of the light sources, wherein the light irradiation unit further comprises a light splitting member configured to split light from the light source to the container installation sections,
a plurality of the light reception units are provided corresponding to the container installation sections and configured to detect light split to each of the container installation sections by the light splitting member,
the controller configured to sequentially control the light sources, one by one, to periodically emit light,
the analysis unit configured to create time-series data corresponding to the light sources from detection signals periodically outputted from the light reception part corresponding to the container installation section with the container installed therein, and
the analysis unit configured to analyze the sample with selecting the time-series data suited to a measurement item for the sample in the container installed in the container installation section from among the created time-series data.

16. The blood coagulation analyzer according to claim 15, wherein
the controller configured to continue the control of sequentially causing the light sources, one by one, to periodically emit light at least for a time period between when the analyzer is set in a standby state and when a shut-down instruction is received.

17. The blood coagulation analyzer according to claim 15, further comprising:
a catcher mechanism configured to catch the container and to install the container in any of the container installation sections and,
a disposal port into which the container is to be discarded, wherein
the controller is configured to control the catcher mechanism such that the catcher mechanism installs the container storing the measurement specimen in the container installation section, takes the container out of the container installation section after the elapse of a measurement time corresponding to a measurement item of the sample in the container installed in the container installation section, and discards the container into the disposal port.

18. The blood coagulation analyzer according to claim 15, wherein
in the case that the measurement item of the sample in the container installed in the container installation section is for blood coagulation measurement, the analysis unit calculates a coagulation time and a concentration or activity of components contained in the sample from the time-series data corresponding to the first wavelength,
in the case that the measurement item of the sample in the container installed in the container installation section is for synthetic substrate measurement, the analysis unit calculates a concentration or activity of components contained in the sample from the time-series data corresponding to the second wavelength, and
in the case that the measurement item of the sample in the container installed in the container installation section is for immunonephelometry measurement, the analysis unit calculates a concentration or activity of components contained in the sample from the time-series data corresponding to the third wavelength.

19. The blood coagulation analyzer according to claim 1, further comprising:
a controller that controls operations of the light sources; and a reference light reception part that is provided in addition to the light reception part, and receives light applied from the light irradiation unit and not transmitted through the container, wherein the controller controls a current value to be supplied to the light source in reference to a detection signal obtained by the reference light reception part.

20. The blood coagulation analyzer according to claim 1, wherein the light source comprises an LED.

21. The blood coagulation analyzer according to claim 1, wherein the light sources further include a fourth light source configured to generate light of a fourth wavelength different from the second wavelength for synthetic substrate measurement.

22. The blood coagulation analyzer according to claim 21, wherein the optical fiber parts are gathered to and bundled along an optical fiber part corresponding to the fourth light source, and the optical fiber part corresponding to the fourth light source is shortest in length from the incident end to the exit end among the optical fiber parts corresponding to the first to fourth light sources.

23. The blood coagulation analyzer according to claim 1, wherein the light sources further include a fifth light source configured to generate light of a fifth wavelength different from the third wavelength for immunonephelometry measurement.

24. A blood coagulation analyzing method comprising:

generating light from light sources including a first light source configured to generate light of a first wavelength for blood coagulation time measurement, a second light source configured to generate light of a second wavelength for synthetic substrate measurement, and a third light source configured to generate light of a third wavelength for immunonephelometry measurement, wherein the respective light sources are held by light source holders;

making the lights from the light sources incident on incident ends of optical fiber parts, wherein the incident ends of the optical fiber parts are held by incident end holders such that the incident ends face the respective light sources;

applying light emitted from each of exit ends of the optical fiber parts onto a container configured to contain a measurement specimen storing a sample and a reagent;

detecting light transmitted through the container so as to analyze the sample using the detected light.

25. A blood coagulation analyzer comprising:

a first light source configured to generate light having a wavelength of 620 nm to 690 nm which is applied to blood coagulation time measurement, a second light source configured to generate light having a wavelength of 390 nm to 420 m which is applied to synthetic substrate measurement, a third light source configured to generate light having a wavelength of 690 nm to 820 nm which is applied to immunonephelometry measurement;

light source holders holding the first to third light sources;

optical fibers, arranged correspondingly to respective light sources, each configured to lead light from one end to the other end, the one end being held by an incident end holder such that a center axis of the optical fiber is aligned with an optical axis of corresponding light source, and the other end being arranged to emit the light led through the optical fiber onto a container storing a measurement specimen prepared from a sample and a reagent;

a light reception part configured to receive light transmitted through the container; and a computer configured to analyze a data generated based on electric signal outputted from the light reception part.

* * * * *